US012758258B2

(12) United States Patent
Belson et al.

(10) Patent No.: US 12,758,258 B2
(45) Date of Patent: Oct. 13, 2026

(54) APPARATUS AND METHODS FOR HYBRID ENDOSCOPIC AND LAPAROSCOPIC SURGERY

(71) Applicant: Modular Surgical, Inc., Dania Beach, FL (US)

(72) Inventors: Amir Belson, Savyon (IL); James J. Leary, St. Louis, MO (US)

(73) Assignee: Modular Surgical, Inc., Cupertino, CA (US)

( * ) Notice: Subject to any disclaimer, the term of this patent is extended or adjusted under 35 U.S.C. 154(b) by 0 days.

(21) Appl. No.: 18/438,091

(22) Filed: Feb. 9, 2024

(65) Prior Publication Data

US 2024/0366262 A1 Nov. 7, 2024

Related U.S. Application Data

(63) Continuation of application No. 17/133,551, filed on Dec. 23, 2020, now abandoned, which is a
(Continued)

(51) Int. Cl.
*A61B 17/34* (2006.01)
*A61B 1/00* (2006.01)
(Continued)

(52) U.S. Cl.
CPC ...... *A61B 17/3423* (2013.01); *A61B 1/00087* (2013.01); *A61B 1/044* (2022.02);
(Continued)

(58) Field of Classification Search
CPC .... A61B 17/00234; A61B 2017/00292; A61B 2017/00296; A61B 2017/00367;
(Continued)

(56) References Cited

U.S. PATENT DOCUMENTS 4,991,270 A 2/1991 Aok
5,925,002 A 7/1999 Wollman
(Continued)

FOREIGN PATENT DOCUMENTS

WO WO2008/015666 A2 2/2008
WO WO2010/098871 A2 9/2010

OTHER PUBLICATIONS

Banihani et al.; Plug-and-play tool handles for laparoscopic surgery simulators; Rensselaer Polytechnic Institute; Computer-Aided Engineering; Vil. 1; pp. 6-3; Jan. 1, 2009.
(Continued)

*Primary Examiner* — Ahmed M Farah
(74) *Attorney, Agent, or Firm* — Shay Glenn LLP

(57) ABSTRACT

Apparatus and methods are described allow the techniques of endoscopic and laparoscopic surgery to be combined into a minimally invasive hybrid surgical technique called NOTES-assisted laparoscopic surgery. Manual and robotic-controlled versions of a modular laparoscopic tool are described having a small diameter shaft that is delivered laparoscopically to a surgical site. Larger diameter working tips are delivered through a NOTES delivery tube inserted to the surgical site through a natural orifice and joined to the shaft of the modular laparoscopic tool. Larger diameter working tips improve the effectiveness of the modular laparoscopic tools and the number and size of laparoscopic ports used can also be reduced.

1 Claim, 32 Drawing Sheets

Related U.S. Application Data continuation of application No. 14/338,237, filed on Jul. 22, 2014, now Pat. No. 10,898,173, which is a continuation of application No. 13/728,930, filed on Dec. 27, 2012, now Pat. No. 8,827,988, which is a continuation of application No. 13/380,198, filed as application No. PCT/US2010/000584 on Feb. 26, 2010, now abandoned.

(60) Provisional application No. 61/275,360, filed on Aug. 28, 2009, provisional application No. 61/216,304, filed on May 14, 2009, provisional application No. 61/208,793, filed on Feb. 27, 2009.

(51) Int. Cl.

| | |
|---|---|
| ***A61B 1/04*** | (2006.01) |
| ***A61B 1/313*** | (2006.01) |
| ***A61B 1/32*** | (2006.01) |
| ***A61B 17/00*** | (2006.01) |
| ***A61B 17/02*** | (2006.01) |
| ***A61B 17/04*** | (2006.01) |
| ***A61B 17/29*** | (2006.01) |
| ***A61B 17/3201*** | (2006.01) |
| ***A61B 34/30*** | (2016.01) |
| ***A61B 34/37*** | (2016.01) |
| ***A61B 90/00*** | (2016.01) |
| *A61B 90/30* | (2016.01) |

(52) U.S. Cl.

CPC .............. *A61B 1/3132* (2013.01); *A61B 1/32* (2013.01); *A61B 17/00* (2013.01); *A61B 17/00234* (2013.01); *A61B 17/0218* (2013.01); *A61B 17/0469* (2013.01); *A61B 17/29* (2013.01); *A61B 17/3201* (2013.01); *A61B 34/30* (2016.02); *A61B 34/37* (2016.02); *A61B 90/361* (2016.02); *A61B 2017/00278* (2013.01); *A61B 2017/00362* (2013.01); *A61B 2017/00411* (2013.01); *A61B 2017/00464* (2013.01); *A61B 2017/00477* (2013.01); *A61B 2017/00539* (2013.01); *A61B 2017/00544* (2013.01); *A61B 2017/00876* (2013.01); *A61B 17/0483* (2013.01); *A61B 2017/2901* (2013.01); *A61B 2017/2902* (2013.01); *A61B 2017/2931* (2013.01); *A61B 2017/2943* (2013.01); *A61B 2090/306* (2016.02); *A61B 2090/3614* (2016.02)

(58) Field of Classification Search

CPC .... A61B 2017/0042; A61B 2017/0046; A61B 2017/00464; A61B 2017/00477; A61B 2017/00876; A61B 17/32; A61B 17/320016; A61B 17/3211; A61B 17/3213; A61B 17/29; A61B 2017/2901; A61B 2017/2909; A61B 2017/2931; A61B 2017/2939; A61B 2017/294; A61B 1/00064; A61B 1/00066; A61B 1/00071; A61B 1/00087; A61B 1/313; A61B 1/3132; A61B 17/3423; A61B 2017/0034

USPC ........................................................ 600/109

See application file for complete search history.

(56) References Cited

U.S. PATENT DOCUMENTS

| | | | | |
|---|---|---|---|---|
| 5,935,126 | A * | 8/1999 | Riza | A61B 17/2909 606/51 |
| 6,048,073 | A | 4/2000 | Shiao | |
| 6,309,397 | B1 | 10/2001 | Julian et al. | |
| 7,039,975 | B1 | 5/2006 | Liao | |
| 7,492,116 | B2 * | 2/2009 | Oleynikov | A61B 34/70 600/101 |
| 7,691,126 | B2 | 4/2010 | Bacher | |
| 8,353,897 | B2 | 1/2013 | Doyle et al. | |
| 8,469,972 | B2 * | 6/2013 | Harris | A61B 17/00234 606/1 |
| 8,747,394 | B2 | 6/2014 | Belson et al. | |
| 8,827,988 | B2 * | 9/2014 | Belson | A61B 17/3201 606/49 |
| 8,858,538 | B2 | 10/2014 | Belson et al. | |
| 8,858,638 | B2 | 10/2014 | Michelson | |
| 10,166,030 | B2 | 1/2019 | Newell et al. | |
| 10,898,173 | B2 * | 1/2021 | Belson | A61B 1/00087 |
| 2002/0107533 | A1 | 8/2002 | Solingen | |
| 2003/0114731 | A1 | 6/2003 | Cadeddu et al. | |
| 2005/0043718 | A1 | 2/2005 | Madhani et al. | |
| 2005/0165449 | A1 | 7/2005 | Cadeddu et al. | |
| 2005/0209607 | A1 | 9/2005 | Lipchitz et al. | |
| 2005/0283150 | A1 | 12/2005 | Moutafis et al. | |
| 2006/0020213 | A1 * | 1/2006 | Whitman | A61B 1/05 600/478 |
| 2006/0020287 | A1 | 1/2006 | Lee et al. | |
| 2006/0041243 | A1 | 2/2006 | Nayak et al. | |
| 2006/0041273 | A1 | 2/2006 | Ortiz et al. | |
| 2006/0161045 | A1 | 7/2006 | Merril et al. | |
| 2006/0178672 | A1 | 8/2006 | Shores et al. | |
| 2007/0198000 | A1 | 8/2007 | Miyamoto et al. | |
| 2007/0233130 | A1 | 10/2007 | Suddaby | |
| 2008/0021274 | A1 | 1/2008 | Bayer et al. | |
| 2008/0108869 | A1 * | 5/2008 | Sanders | A61B 1/00124 600/109 |
| 2008/0108871 | A1 | 5/2008 | Mohr | |
| 2008/0147096 | A1 | 6/2008 | Azonian et al. | |
| 2008/0167672 | A1 | 7/2008 | Giordano et al. | |
| 2008/0242939 | A1 | 10/2008 | Johnston | |
| 2008/0243106 | A1 * | 10/2008 | Coe | A61B 17/00234 606/1 |
| 2008/0275480 | A1 | 11/2008 | Jacobs et al. | |
| 2009/0005635 | A1 | 1/2009 | Zhang et al. | |
| 2009/0005638 | A1 | 1/2009 | Zwolinski | |
| 2009/0171373 | A1 * | 7/2009 | Farritor | A61B 34/30 606/130 |
| 2009/0182193 | A1 | 7/2009 | Whitman et al. | |
| 2009/0209947 | A1 | 8/2009 | Gordin et al. | |
| 2010/0016855 | A1 | 1/2010 | Ramstein et al. | |
| 2010/0057078 | A1 | 3/2010 | Arts et al. | |
| 2010/0094116 | A1 | 4/2010 | Silverstein | |
| 2010/0188493 | A1 | 7/2010 | Kanzaki et al. | |
| 2010/0217245 | A1 | 8/2010 | Prescott | |
| 2010/0298645 | A1 | 11/2010 | Deutch | |
| 2011/0087267 | A1 | 4/2011 | Spivey | |
| 2011/0288560 | A1 | 11/2011 | Shohat et al. | |
| 2012/0083826 | A1 | 4/2012 | Chao et al. | |
| 2012/0132450 | A1 | 5/2012 | Timm et al. | |
| 2013/0066304 | A1 | 3/2013 | Belson et al. | |
| 2019/0183515 | A1 | 6/2019 | Newell et al. | |
| 2020/0085508 | A1 * | 3/2020 | O'Hara | A61B 34/32 |
| 2022/0008047 | A1 | 1/2022 | Belson et al. | |
| 2025/0009467 | A1 | 1/2025 | Peterson et al. | |

OTHER PUBLICATIONS

Newell et al.; U.S. Appl. No. 18/907,384 entitled "Surgical tool system having multiple tool tip interfaces," filed Oct. 4, 2024.

* cited by examiner

APPARATUS AND METHODS FOR HYBRID ENDOSCOPIC AND LAPAROSCOPIC SURGERY

CROSS-REFERENCE TO RELATED APPLICATIONS

The present application is a continuation of U.S. patent application Ser. No. 17/133,551, filed Dec. 23, 2020, now U.S. Patent Application Publication No. 2022/0008047, which is a continuation of U.S. patent application Ser. No. 14/338,237, filed Jul. 22, 2014, now U.S. Pat. No. 10,898, 173, which is a continuation of U.S. patent application Ser. No. 13/728,930, filed Dec. 27, 2012, now U.S. Pat. No. 8,827,988, which is a continuation of U.S. patent application Ser. No. 13/380,198, filed Dec. 22, 2011, which is a 371 National Stage Application of PCT Application No. PCT/US2010/000584, filed Feb. 26, 2010, which claims priority from Provisional Patent Application No. 61/208,793, filed on Feb. 27, 2009; Provisional Patent Application No. 61/216,304, filed on May 14, 2009; and Provisional Patent Application No. 61/275,360, filed on Aug. 28, 2009, the full disclosures of which are incorporated herein by reference.

BACKGROUND OF THE INVENTION

Field of the Invention

The present invention relates generally to apparatus and methods for performing surgery. In particular, it relates to apparatus and methods that combine the techniques of endoscopic and laparoscopic surgery in a minimally invasive hybrid surgical technique. The apparatus and methods of the invention can be implemented using manual or robotic instruments.

Laparoscopy was an evolution from open abdominal surgery. Laparoscopy offered faster recovery, reduction in pain and less scarring post surgery. Compared with open surgery, where the surgeon manipulates the tissue and performs the surgery when the entire surgical field is exposed, the laparoscopic procedure required significant training. The learning curve was slow and it took a large number of procedures to be performed before the surgeon mastered the mental, as well as manual, demands of the technique and the procedure time was shortened.

In the last few years, as part of the tendency to perform less invasive procedures surgeons started performing natural orifice transluminal endoscopic surgeries (NOTES) where the scope is introduced to the peritoneal space via the stomach, anus, vagina or umbilicus. This approach eliminates the need to cross the skin and the musculature to get to the peritoneal space, which reduces the pain even further, helps cosmetically and may even help to reduce the adhesion rate.

The problem is that this approach requires the use of flexible and controllable delivery platforms and endoscopes so that they can navigate in the tortuous path of the GI tract and in between organs in the peritoneum. Those devices need to be stiff enough during tissue manipulation, but flexible enough when passing in the GI tract, vagina or colon. For surgeons that are used to laparoscopy (rigid tools), it is not easy to get used to the image during endoscopy, particularly during retroflection with flexible endoscopes.

One of the big advantages that transluminal surgery has to offer is the ability to extract big bulks of tissue or organs through the opening in the stomach, vagina or colon without causing more pain.

Because of the technical challenges involved and the lack of appropriate tools, most of the NOTES surgeries reported in the medical literature have been performed using hybrid procedures that combine endoscopic and laparoscopic surgical techniques (also described as endo-laparoscopic surgery) or using transvaginal access in upper abdominal surgeries and transgastric in lower abdominal procedures. Many of the pioneers in NOTES surgery consider this hybrid approach to be only an intermediate step or a bridge to true endoscopic NOTES surgery, their stated goal being to entirely eliminate the laparoscopic component of the surgery. To the present inventor, however, this approach seems idealistic and somewhat short sighted. Greater advantages can be achieved for the benefit of the patient and the convenience of the surgeon by retaining the laparoscopic component, while minimizing the invasiveness and simultaneously improving the effectiveness of the laparoscopic tools used. This can be achieved by utilizing modular laparoscopy tools with very thin shafts to minimize the puncture size needed to insert the tools through the abdominal wall and using the NOTES endoscope working channel or an overtube or tube as a conduit to deliver the larger diameter working tips of the modular laparoscopy tools that will attach to the shaft or shafts inside the body. Alternatively, a single larger laparoscopic cannula can be used to deliver the larger diameter working tips of the modular laparoscopy tools to the surgical site. For this approach, the preferred location can be the umbilicus—for better cosmetic outcome.

If laparoscopy or thoracoscopy would employ very small tools (in the range of 2-5 mm) then pain will be significantly reduced and so also will be the risk for hernia at the incision site.

SUMMARY OF THE INVENTION

This patent describes the combination of natural orifice transluminal endoscopic surgery (NOTES) with small laparoscopic instruments (with very small shafts). The patent describes a way to maintain the laparoscope instruments' surgical abilities and operating techniques with the reductions of its size.

The invention provides a modular laparoscopic surgery tool with a small shaft that is introduced through the skin either directly or through a trocar sheath and that connects to a tip that is delivered through another port, either through the skin or through a natural orifice, where the shaft moves the tip in space and controls the actuation of the tip or delivers the tip to a target location and secures it there.

The invention also provides a modular laparoscopic surgery tool with a connector that is easy to connect and disconnect, that connects a small shaft to a bigger tip where the connector either delivers the actuation force needed for the actuation of the tip and/or delivers the energy required for an actuation element that is located inside the tip and/or delivers control signals to a tip that has both an actuation element (like a motor) and energy source (like a battery) where the shaft also holds the tip in space and moves the entire tip from one spot to another in space.

The shaft of the modular laparoscopic surgery tool will optionally include both actuation means or energy delivery means or control signal delivery means and a rigid structure that holds and moves the tip around.

Optionally, the connector will enable transfer of hydraulic force from the shaft to the tip while also controlling the tip's position in space and moving it around.

Optionally, the connector will enable transfer of pneumatic force from the shaft to the tip while also controlling the tip's position in space and moving it around.

Optionally, the connector will enable transfer of rotation force from the shaft to the tip while also controlling the tip's position in space and moving it around.

Optionally, the connector will enable transfer of mechanical push force from the shaft to the tip while also controlling the tip's position in space and moving it around. Optionally, the connector will enable transfer of magnetic force from the shaft to the tip while also controlling the tip's position in space and moving it around.

Optionally, the connector will enable transfer of electrical energy from the shaft to the tip while also controlling the tip's position in space and moving it around.

Optionally, the connector will enable transfer of any other type of energy, such as RF, etc. from the shaft to the tip while also controlling the tip's position in space and moving it around.

Optionally, the connector will enable transfer of light from the shaft to the tip or image from the tip to the shaft while also controlling the tip's position in space and moving it around.

Optionally, the connector will enable transfer of digital image signals from the tip to the shaft while also controlling the tip's position in space and moving it around.

The system may include a stereoscopic image module to provide the operator with a three dimensional image.

In one embodiment, a camera will be delivered with the other tips through a port different than the shaft port. Optionally, the camera may provide stereoscopic imaging. The shaft may then connect to the camera and deliver it to a preferred location and then anchor it at the preferred location (like the abdominal wall). The shaft then will disconnect from the camera. The camera may be connected to the image processor with a wire that will run through the overtube, through another port or will transmit the images wirelessly or through a small cable through the abdominal wall (or small needle). Optionally, the camera may be anchored against the abdominal wall using an external magnet. A motor or other actuator may be used to aim the camera via remote control or thorough an umbilical cable after it is in place and to control the zoom in and zoom out. This same method may be used for insertion and placement of one or more illumination devices into the surgical site. The system may use magnetic energy or RF energy or any other type of energy that will cross the abdominal wall and energize the camera and or the lights. The first engagement of the shaft and the camera can also be visualized through a small needle through the skin or using a fiber optic cable that will run in or along the shaft.

In order to connect the shaft to the camera at the start of the procedure, images of the approaching shaft (to the camera) may be visualized via the camera that is delivered with the tips or via an optic fiber that will run in or outside the shaft.

The camera and/or the light projectors will have means for easy attachment and detachment to and from the internal abdominal wall (active or passive). In the same way, a light source, based on optic fibers will deliver light from the outside or LEDs that will get their energy through a cable that will run through the overtube or another port. They may also have batteries. They may also be energized through charging energy that will be delivered through the abdominal wall. The tip will carry the light source and will anchor it in a preferred location, such as the internal abdominal wall.

One of the tips that will be delivered through the overtube or separate port may be an ultrasound transducer that will be carried to the desired location using the thin shaft. This transducer may be connected to the outside with a cable that will deliver the signals to the processor.

A different tip that may be delivered to the site in the same way may be a projector that may project on the internal organs images that were taken in earlier imaging studies. For example, the projector, which will be a tip that will be delivered, could be attached to the internal abdominal wall and project a CT image of the liver on the actual liver so that the operator will be able to know where is the location of internal findings in the liver that were found in a prior imaging study.

In yet another example, the overtube may be used to deliver clips, sutures, loops, needles and other accessories that will be needed for the surgery and may be employed or deployed by a tip that was also delivered the same way.

The camera or the light source may be held in place and be manipulated using a magnet that will be held outside the abdomen.

Optionally, the connector will enable transfer of rotational force form the shaft to the tip while also controlling the tip's position in space and moving it around. Optionally, the connector will enable delivery of electric signals from the shaft to actuation motors that will be housed in the tip and will actuate the tip while also controlling the tip's position in space and moving it around.

The connector will hold the tip stable relative to the shaft and will essentially make the shaft and tip one unit such that the tip will be carried in space while connected to the distal shaft and according to the movement that the operator gives the handle.

The shaft may be made of a single rigid unit or may have a controllable distal part or another part proximal to the distal part, in such a way that the operator will be able to steer the distal part of the shaft so that it will have a position with some angle different than 180 degrees from the proximal shaft.

The shaft could be hollow or solid and could potentially have a telescopic structure.

Unlike prior art, the current shaft may connect to different tips, move them in space and actuate them during a single surgery.

In one option, different small shafts will be used for different tips. The different tool shaft will be exchanged during the surgery as needed. For example when a grasper is needed, a grasping shaft will be inserted through the skin or through a trocar sheath and connect inside the abdominal cavity to a grasping tip. Then, if an electrocautery tool will be needed, the grasping tip will be separated from the shaft in the abdomen, the grasper shaft will be withdrawn and an electrocautery shaft will be inserted, preferably through the same hole.

In another option, the external shaft will stay in place and the internal part, which in one example actuates the tip, will be exchanged with the handle controlling actuation of the new tip.

In a preferred example, a single shaft will be able to control different tips so that the shaft will not have to be exchanged.

Preferably, the step of connecting the tip to the shaft can be performed away from abdominal wall and with no need for contact with the abdominal wall.

Preferably the tip will be able to manipulate the tissue at or close to the organ bed without the need to move the organ or tissue away from the organ bed.

In a manually operated version of the modular laparoscopic surgery tool, a handle connected to the proximal end of the shaft will be controlled by the operator directly allowing the operator to actuate the working tip, as well as to control the tip's position in space and move it around. The handle can be translated and rotated as well as inserted and withdrawn to manually control the position of the tip in three dimensions.

In a robotically operated version of the modular laparoscopic surgery tool, the working tip of the tool may be configured with a robotic end effector that is operated through the shaft of the tool, which is connected to a robotic surgical system located outside of the patient's body. Also, the shaft may be controlled and manipulated in space robotically.

Alternatively, in a robotically operated version of the modular laparoscopic surgery tool, the working tip of the tool may be configured with a robotic end effector that is operated remotely in a master/slave relationship with a robotic surgical system.

In the robotic version of the invention the operator may not physically touch the handle or the proximal shaft but rather work from a remote working station in a master slave fashion.

The different tips will be delivered through the overtube, tube or endoscope one at a time or more preferably the tips will be housed in a mechanical structure (cassette) and be delivered together to the abdominal space or thoracic space. The cassette will optionally have a structure (like legs or a base) that will enable a stable position in the peritoneal cavity on top of the different organs.

In addition to hybrid NOTES-assisted laparoscopic surgery, many of the methods and apparatus described herein can also be used to facilitate other surgical approaches, including, but not limited to NOTES-assisted NOTES surgery, where two or more NOTES devices are inserted through different bodily orifices to a surgical site. Working tips can be inserted through one of the NOTES devices and another NOTES device with an elongated shaft like the laparoscopic tools described herein can be inserted through the other NOTES device, optionally being inserted through the wall of an internal organ into the thoracic or abdominal cavity. The working tip can be joined to the elongated shaft inside of the body cavity. This approach can minimize the size and number of internal incisions that must be made for surgical access, just as the hybrid NOTES-assisted laparoscopic surgery can minimize the size and number of laparoscopic ports that are made.

BRIEF DESCRIPTION OF THE DRAWINGS

FIG. 4 illustrates positive pressure used to insert the tip in.

DETAILED DESCRIPTION OF THE INVENTION

Figure 1A:
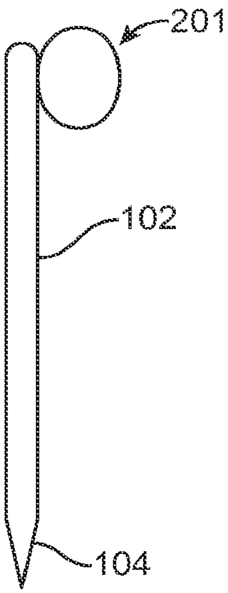
FIGS. 1A-1F show variations of a laparoscopic instrument shaft without the tip.
Figure 1B:
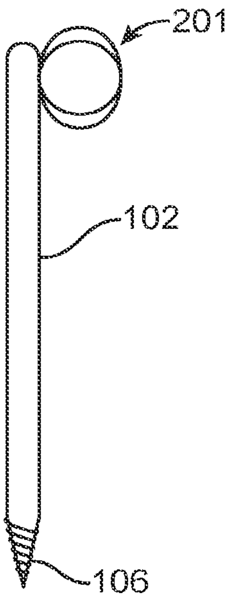
Figure 1C:
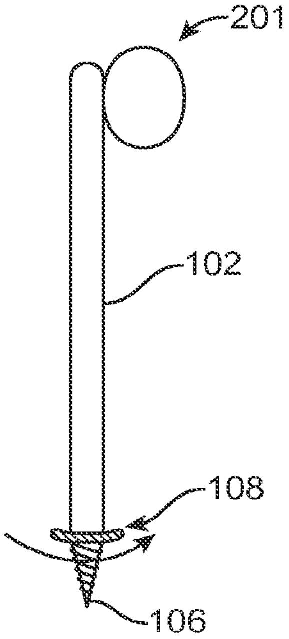

The present invention utilizes small diameter and potentially rigid shafts that will be inserted into the peritoneal or thoracic cavity through the skin (through cannulas or directly through the skin) and then their distal end will be connected to a tip that will be delivered to the peritoneal or thoracic cavity via a NOTES approach. Once this connection will be established, the handle or any other user interface that will be located at the proximal part of the rod or shaft or along the shaft, outside the body, will be able to control the new tip that will be added to the device inside the peritoneal or thoracic cavity. This connection will make the device operable. The tip will then respond to changes that will be applied on the proximal part of the shaft or the tip will deliver information such as images from the space to the proximal part or any other device such a monitor that will be connected to the shaft.

It should be noted that the tip may also be connected to the shaft inside of an organ in the patient's body in order to facilitate internal surgery within the organ. For example, for performing intragastric surgery, the tip can be delivered through the esophagus into the stomach and attached to a shaft inserted through the abdominal wall and through a small opening or incision in the gastric wall into the stomach. Similarly, tips for performing intrauterine surgery can be delivered through the vagina and attached to a shaft inserted laparoscopically into the uterus.

The tip will be delivered through a NOTES approach either through an endoscope or through a tube (like an overtube) that will be placed between the natural orifice and the opening to the peritoneum and potentially will extend a little bit into the peritoneum. The tips that may be inserted to the proximal part of the scope or tube will be pushed manually, robotically, via air pressure or fluid pressure into the peritoneal space. Another option would be to have a pulley at the end of the tube or working channel of the scope or the distal part of the tube and after connecting the tip to the wire (outside the body) the wire will run over the pulley and come back proximally; pulling the wire will bring the tip to the distal end of the tube or scope. At the end of the tube or scope (inside the peritoneum) there may be a net or any other structure that will accept the tip and may host several tips. If air pressure will be used to push the tips in, the net will cover the opening of the working channel of the tube and stop the motion of the tip.

If an overtube is used, it may be placed using an endoscope. Tools that will be delivered via the working channel will be used to open the organ wall (stomach as an example). The scope with the tube around it will be pushed into the peritoneal cavity and the scope may then be pulled outside, leaving the tube in place with its proximal part outside of the body and the distal part in the peritoneum. After the scope is removed, the overtube will be used as a delivery conduit to deliver tips to be attached to the laparoscopy tools. Then, the overtube will be covered (either at its distal orifice, the proximal orifice or in between them) so that the insufflation pressure will not leak. In another option, the tube will be used to constantly deliver more pressure, as needed, to keep the abdominal space insufflated. A valve may be used that allows insertion and removal of the tips or other tools without significant loss of insufflation pressure.

At the end of the surgery if an organ or tissue needs to be taken out, it will be retrieved whole or in pieces through the overtube or the working channels or directly through the natural orifice that was used for access. The tips or tips cassette will also be withdrawn through the overtube, scope or organ directly. One option would be to use suction for quick withdrawal of the tips and tissue.

In order to close the opening in the organ (such as stomach) one option would be to insert the endoscope again through the tube, retract the tube and scope into the organ cavity (such as stomach) and deliver closing endoscopic tools to close the wall). Another option would be to place sutures, such as purse string suture) in the stomach (or other entry organ) wall, around the tube, during the surgery, so that upon retraction of the tube, with or without an endoscope in it, the suture will be tied and the opening will be closed.

There are three stages that are required:

The first is engaging the tip to the shaft. That could be done in several different ways. As an example, magnetic force may be used via a magnet or electromagnet to approximate the tip to the shaft and hold them together as a second optional mechanism will be applied to strengthen the connection. Such force may include torquing a threaded element, like a screw, into an internally threaded structure (like a hole or tube). If a secondary mechanism will be used, the electromagnet could not be used anymore (and the electric power could be discontinued to the electromagnet). Other mechanisms to connect the tip to the shaft could be actuated by motors that may be located within the tip or the shaft. Other mechanisms may include using a key to lock the tip to the shaft. Any other possible connecting mechanism can be used for engaging the tip and the shaft. Optionally, an engagement indicator will be used to indicate to the operator that the connection was successful.

The second is activating the tip to perform the work it is designed to do. This could include opening and closing grasper jaws or scissors, applying electric current in electrocautery or electric cutting, delivering light through a light connector for illumination, carrying a picture or video signal in a laparoscope, opening and closing a basket, opening and closing a stapler and operating the stapler's cutting element, rotating a helical needle, suturing with a suturing device, applying suction through a suction connector or delivering air or other gasses, applying clips to the tissue, delivering other types of energy such as RF or laser or X-rays, actively or passively retracting tissue, opening and closing snares, deliver negative pressure (suction), irrigation, and local insufflations, applying tags or performing any other action that is needed during the surgery and for which the specific tool was designed to do.

The third stage is disconnecting the tip from the shaft. This step will optionally be done inside the net or the mechanism that is used to hold the tip when it is not connected to the shaft (the cassette as an example). Optionally there may be a dedicating mechanism to separate the tip from the shaft, such as: a special "tooth" that will be pushed forward for the separation, air pressure, a bellows, a balloon, torque in the opposite direction or any other possible way.

During this stage, if tissue needs to be evacuated from the surgical field, it could be done through the transluminal access.

An indicator may be used to indicate that the tip is successfully disengaged from the shaft and is successfully engaged in the tip structure.

In general the idea is to use the smallest possible holes in the abdominal wall for minimal scarring and pain and to minimize the risk of hernia and to use the NOTES access to deliver the big tip of the laparoscopic instruments and to retrieve tissue or organs.

Essentially, the surgeon will perform a laparoscopic procedure and the patient will benefit from the NOTES advantages.

The following figures will demonstrate some of the options:

The same principal of connecting a big tip to a small shaft and enabling the tips functionality through the connection could be done when the tip is delivered in another way, not through a NOTES approach, for example through one bigger opening in the skin. In such an approach a single port will be used to deliver bigger trocars or surgical tools and also to deliver big tips that will be connected inside the body to small shafts that will be inserted in a different site.

Figure 1D:
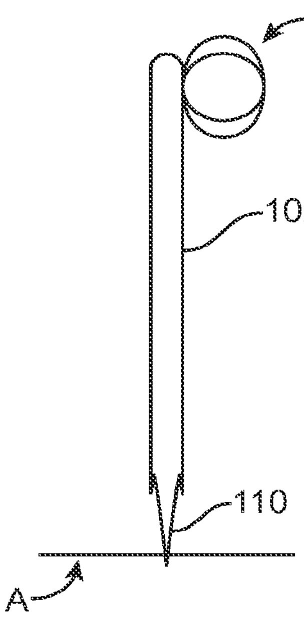
Figure 1E:
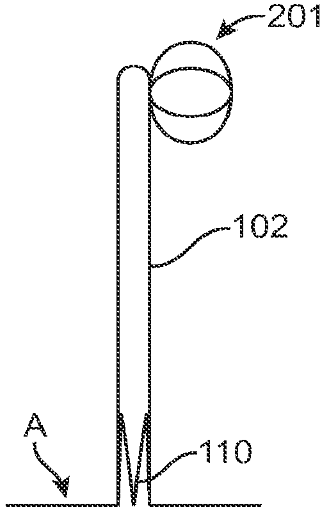
Figure 1F:
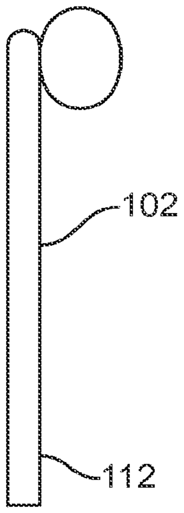

FIGS. 1A-1F show variations of a laparoscopic instrument shaft 102, having handle 201, and without the tip. The distal end 104 of the shaft 102 may be sharp to enable penetration through the abdominal wall A (FIG. 1A), helical or threaded 106 to enable slow and controlled insertion (screwing) through the abdominal wall where the entire shaft will have to be rotated to insert (FIG. 1B) or just the threaded lower part 106 will need to be rotated with a rotating mechanism 108 to insert (FIG. 1C) or using a retractable sharp mechanism 110 for safety (FIG. 1D-IE). It could also be blunt 112 (FIG. 1F) (especially if it is inserted through an introducer).

Figure 2A:
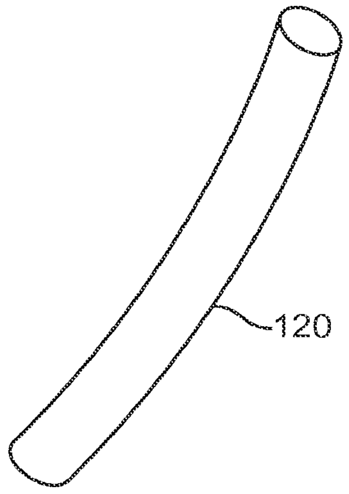
FIGS. 2A-2B show a delivery tube used to deliver the tips to the laparoscopic instrument shaft.
Figure 2B:
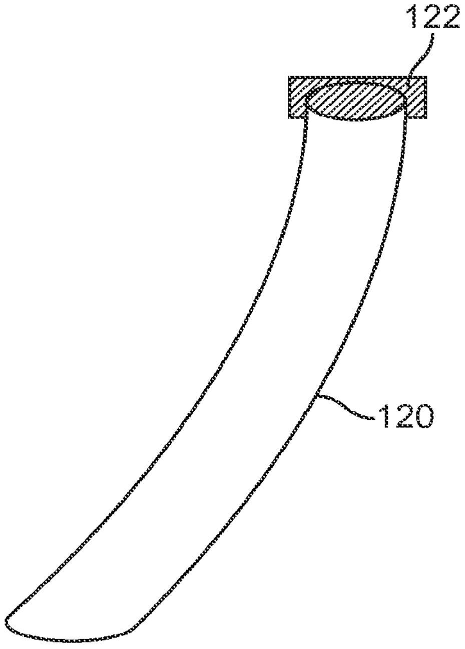

FIG. 2 A shows a delivery tube 120 (optionally configured as an overtube for an endoscope) that will be used to deliver the working tips of the modular laparoscopic surgical tool into the patient's body. As shown in FIG. 2B, a seal 122 or valve may be provided at the proximal end of the delivery tube 120 or another desired location to close the internal lumen and prevent insufflation pressure from leaking after the working tip has been inserted. The tips could be delivered via working channel/s of an endoscope as well. The tube may be continuously used to maintain the desired intra abdominal pressure by delivering extra pressure or evacuating some gas (preferable $CO_2$ or Nitrogen) from the peritoneal cavity. The delivery tube 120 can be rigid, semi rigid or flexible. Optionally, the delivery tube 120 may be expandable or stretchable and collapsible so that it can expand to accommodate the passage of a larger diameter working tip, but can collapse so that it does not occupy the entire body lumen when it is not needed. This will greatly improve patient comfort during surgery performed with NOTES assistance through a delivery tube 120 placed in the patient's esophagus.

Figure 3:
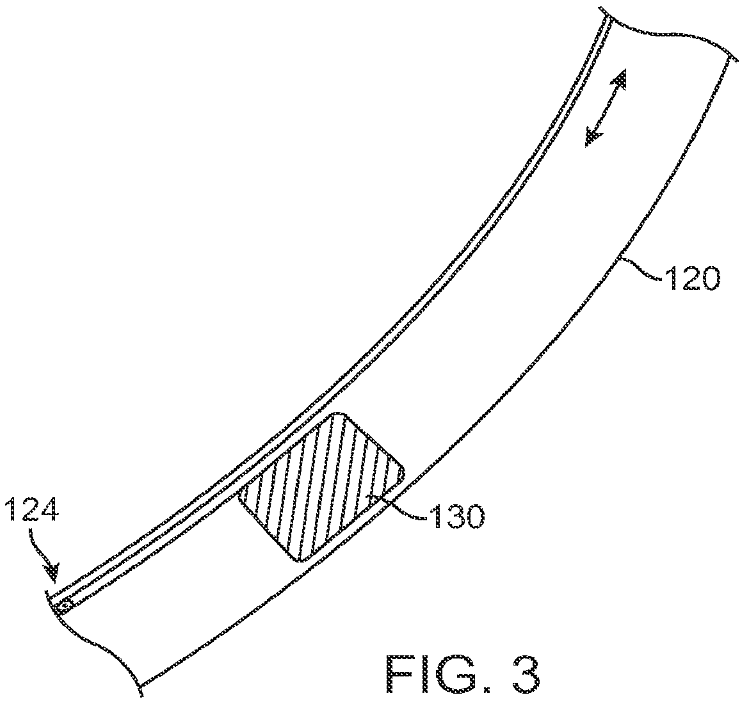
FIG. 3 shows a delivery tube that uses a pulley to bring the tips forward.

FIG. 3 shows a delivery tube 120 that uses a pulley 124 to bring the tips 130 forward.

Figure 4:
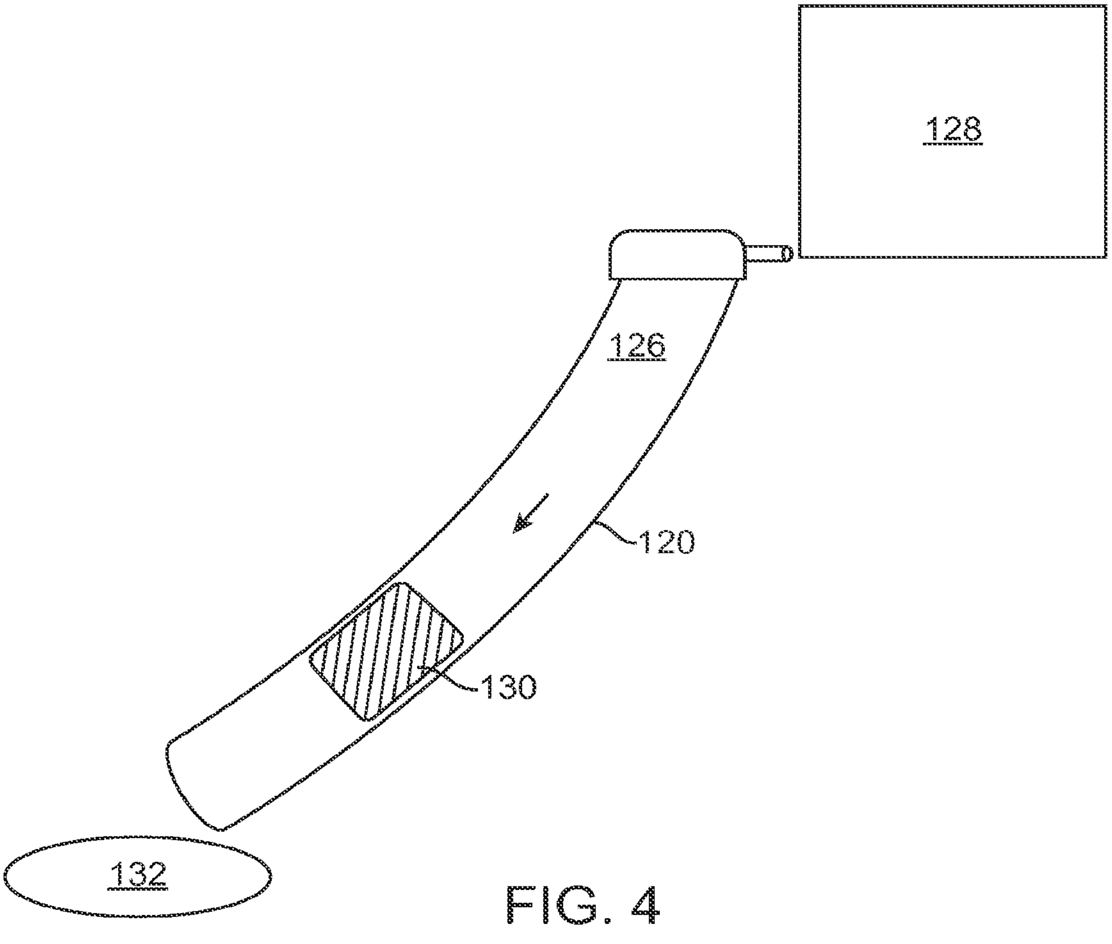

FIG. 4 illustrates positive pressure 126 from a pressure source 128 used to advance the tip 130 through the delivery tube 120. A net 132 may be used to catch the tips at the distal end of the tube.

Figure 5A:
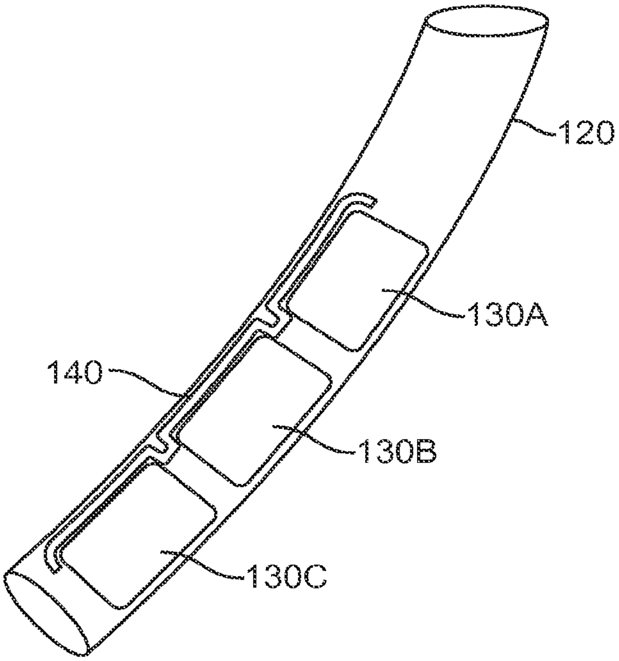
FIGS. 5A-5B show a cassette that may include multiple tips and be delivered into the peritoneal cavity.
Figure 5B:
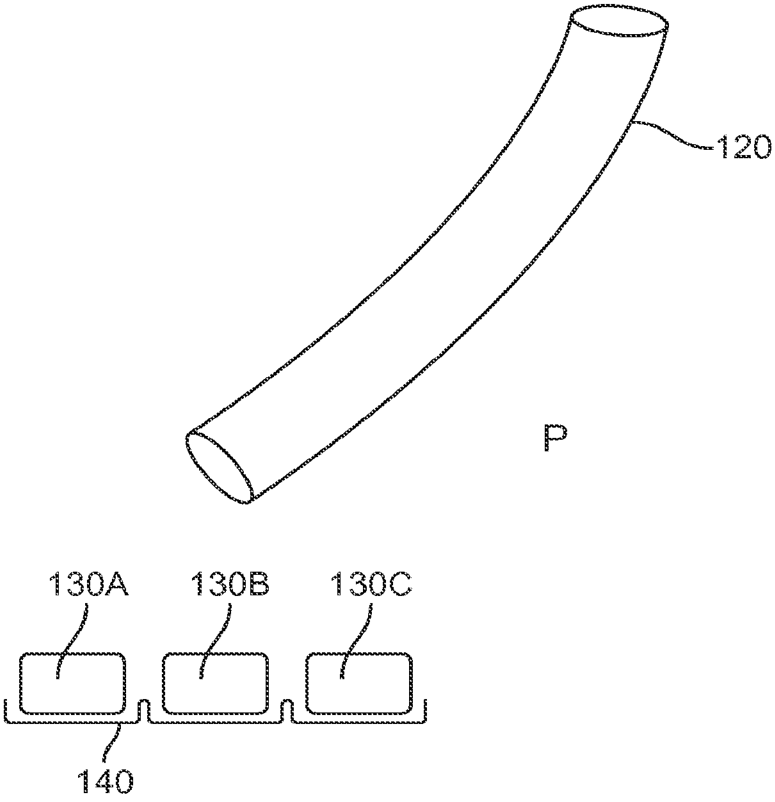

FIGS. 5A-5B show a cassette 140 that may include multiple tips 130A through 130C and be delivered into the peritoneal cavity. FIG. 5 A shows the cassette 140 during delivery. FIG. 5B shows the cassette 140 in the peritoneum P.

Figure 6A:
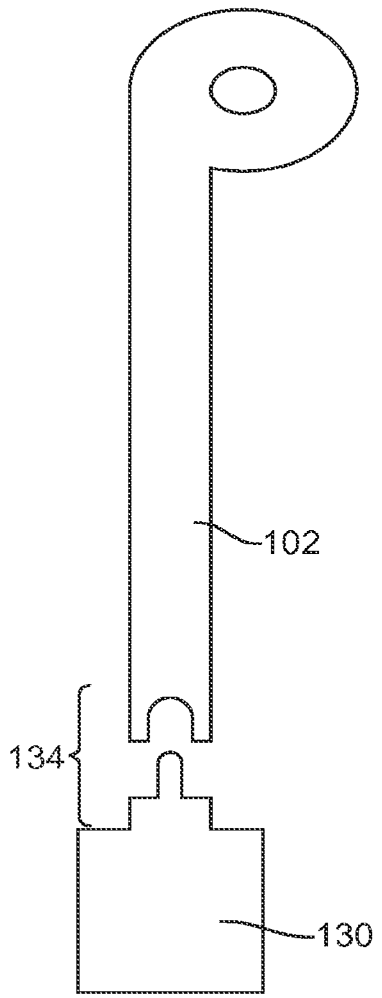
FIGS. 6A-6B illustrate a magnetic connection between the tip and the tube.
Figure 6B:
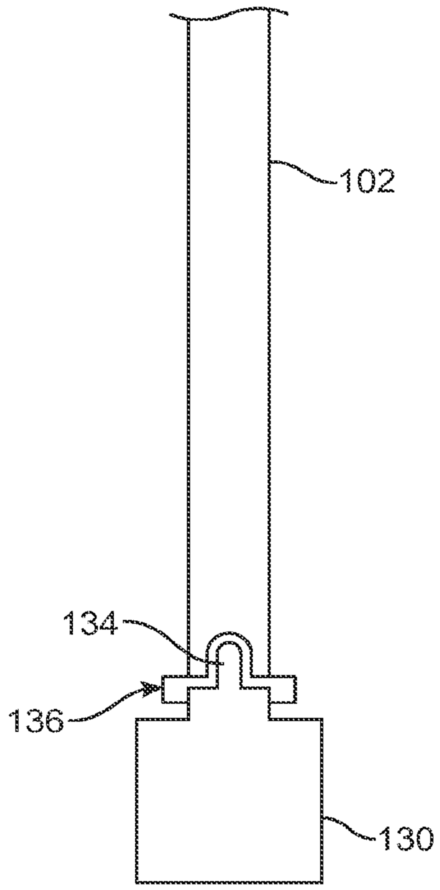

FIGS. 6A-6B illustrate a magnetic connection 134 between the tip 130 and the shaft 102. FIG. 6A shows the magnetic connection being made. FIG. 6B shows the option to create a mechanical connection 136 after the magnetic connection has been made.

Figure 7:
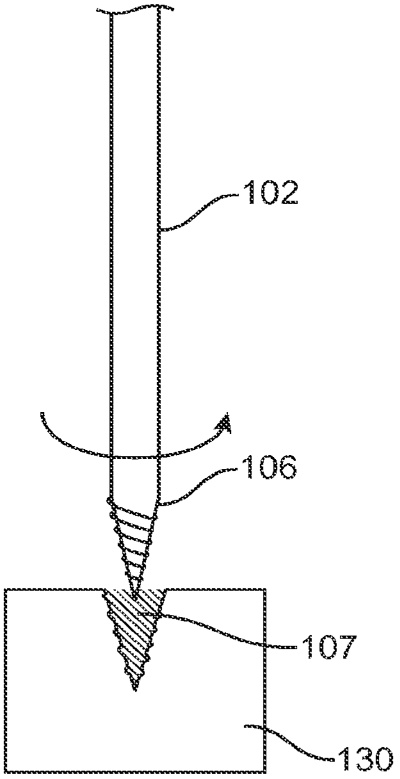
FIG. 7 illustrates a rotation motion that will screw the shaft and the tip together.

FIG. 7 illustrates a rotation motion that will screw a threaded end 106 on the shaft 102 into a threaded receiver 107 in the tip 130 or vice versa. The rotation can be created by rotation of the entire shaft or rotation of part of the shaft. The rotation can be done by a drive shaft that will deliver rotation from the outside, a motor that will be in the tip, a motor in the shaft, pneumatic or hydraulic force.

Figure 8:
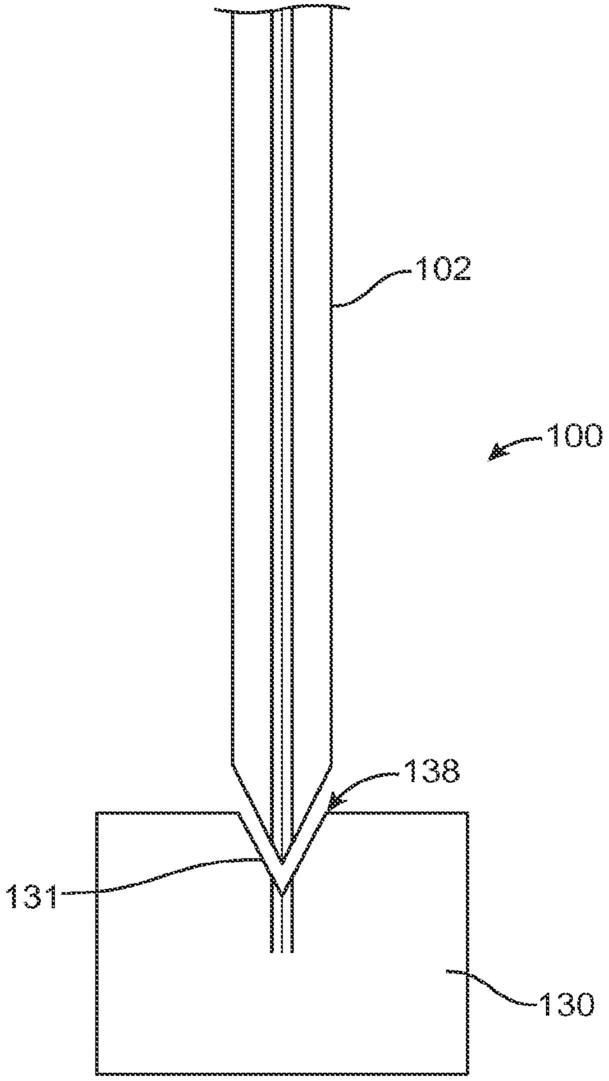
FIG. 8 shows an electric connection between the shaft and the tip.

FIG. 8 shows an electric connection 138 between the shaft 102 and the tip 130 that enables delivery of electrical energy to the tip or deliver energy or signals (like images) back proximally. The electricity could also be used to activate an electroactive polymer based tip. The electric connection 138 may also be used to deliver operation signals to an actuating unit, such as a motor, in the tip. Optionally, in this embodiment and other embodiments of the modular laparoscopic tool 100, the tip 130 may have a tapered or funnel-shaped socket 131 to help align the tip 130 to the shaft 102 during the connection step.

Figure 9:
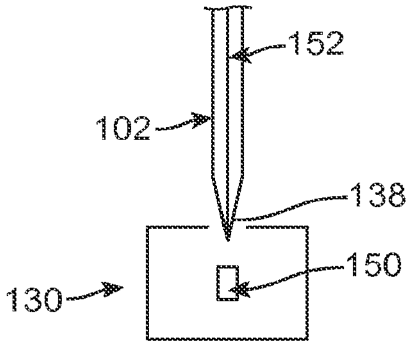
FIG. 9 illustrates a motor located in the tip for tip operation.

FIG. 9 illustrates a motor 150 located in the tip 130 to enable actuation that will be required for the tip operation. The command to the motor 150 and the energy required could potentially run along the shaft 102 and through a connector between the shaft and the tip or through an electrical cable 152 in the shaft 102, if it is hollow.

Figure 10A:
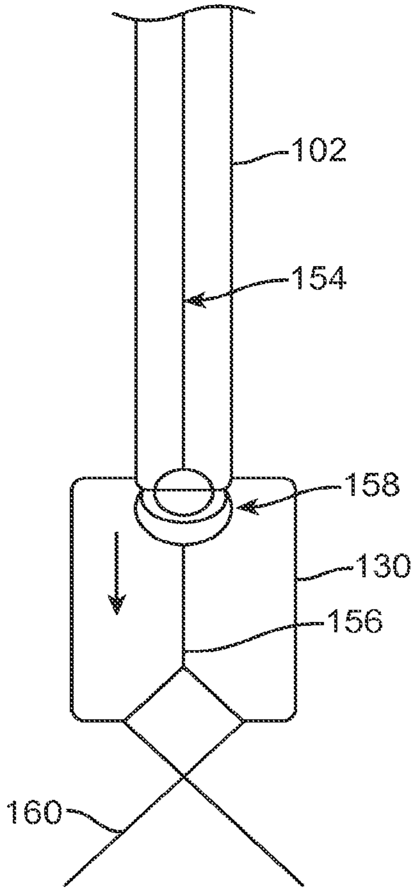
FIGS. 10A-10B illustrates actuation of the tip using a cable in the shaft that connects to a cable in the tip.
Figure 10B:
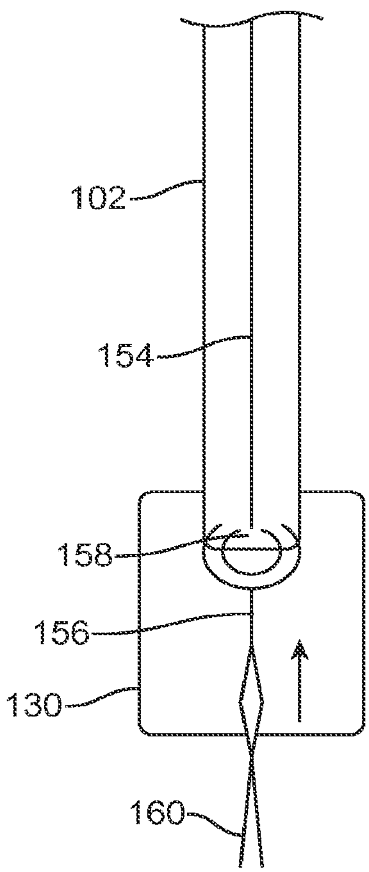

FIGS. 10A-10B illustrate how the actuation of the tip 130 could be delivered using a mechanical cable 154 that will run along the shaft 102 and connect via a connection mechanism 158 to a cable 156 or other actuation mechanism in the tip. An example of a connection mechanism 158 is a magnetic connection, ball and socket, screw etc. Pulling the cable 154 in the shaft 102 will pull the cable 156 in the tip 130 and that will be used for actuation of an end effector 160, such as a grasper.

Figure 11:
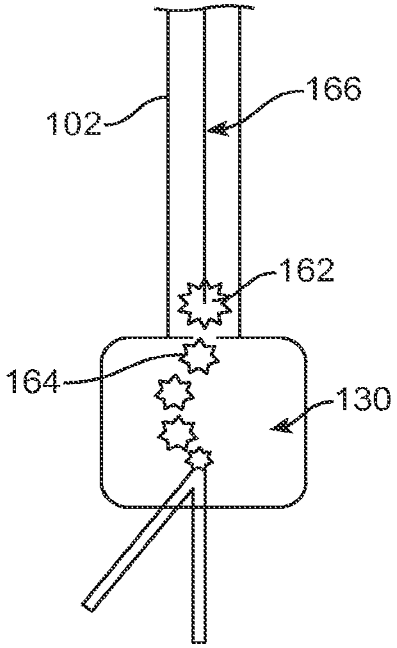
FIG. 11 illustrates tip actuation using a gear system.

FIG. 11 illustrates another example of actuation using a gear system. A gear 162 in the shaft 102 can rotate a gear 164 in the tip 130 once they come in contact. The gear 162 in the shaft 102 can be rotated via air pressure, fluid pressure, drive shaft 166, rotation shaft etc. The gears can generate linear motion, lateral motion and any other direction.

Figure 12A:
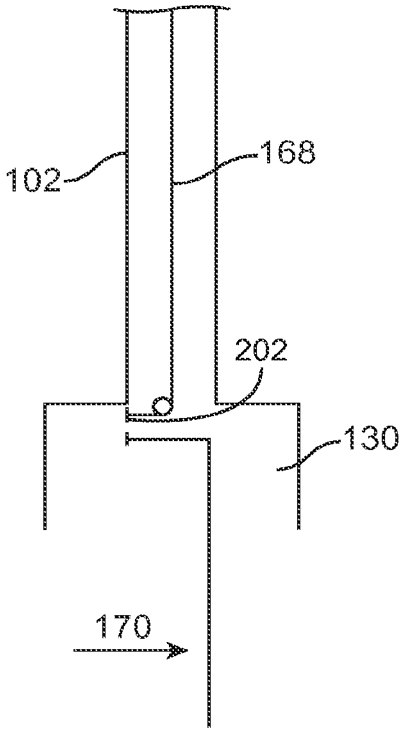
FIGS. 12A-12B illustrate how a lateral motion for tip actuation is generated by pulling a cable that runs along the shaft.
Figure 12B:
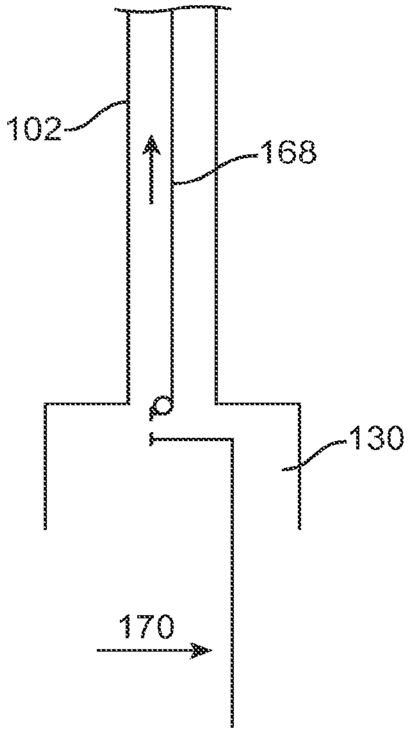

FIGS. 12A-12B illustrates how a lateral motion 170 at the tip 130 (for actuation) can be generated by pulling a cable 168 that runs along the shaft 102 and connector 202.

Figure 13A:
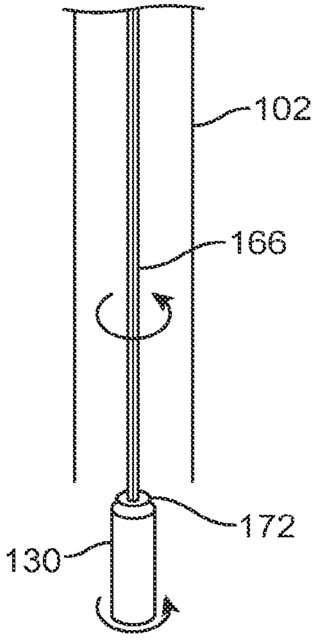
FIGS. 13A-13C show a cable that transmits rotation to the tip through a connector.
Figure 13B:
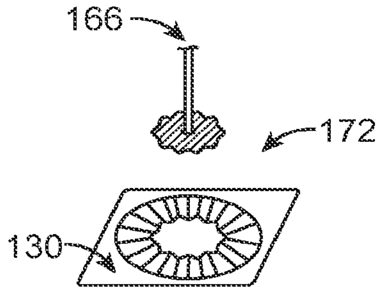
Figure 13C:
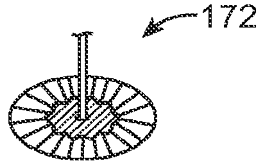

FIG. 13 A shows a drive shaft 166 that can transmit rotation and which is connected to the tip 130 and, through the connector 172, transmits the rotation to the tip 130 for the tip's operation. FIG. 13B shows the connector 172 before engagement. FIG. 13C shows the connector 172 engaged.

Figure 14:
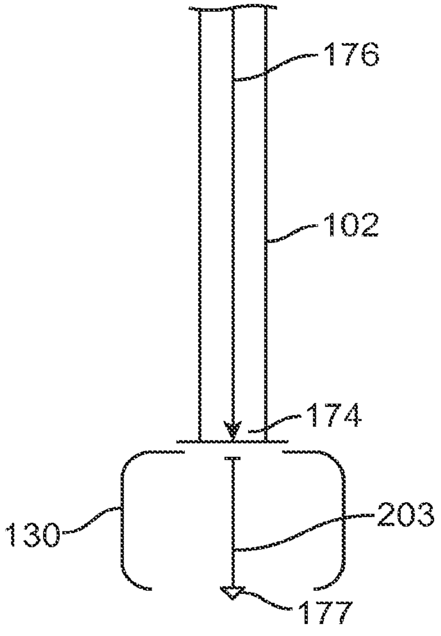
FIG. 14 shows a connector that connects an optic cable that delivers light to the tip.

FIG. 14 shows an optical connector 174 that connects an optic cable 176 to optic cable 203 that delivers light (laser for example) to the tip 130 so that the light will be used for the procedure, for example for laser cutting, ablation or for cautery. The tip may also include a lens 177.

Figure 15A:
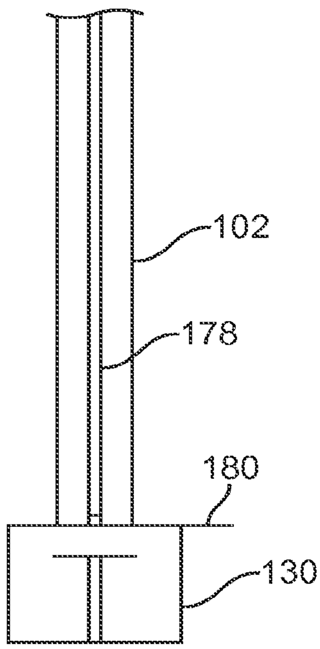
FIGS. 15A-15B show how hydraulic and pneumatic pressure can actuate the tip.
Figure 15B:
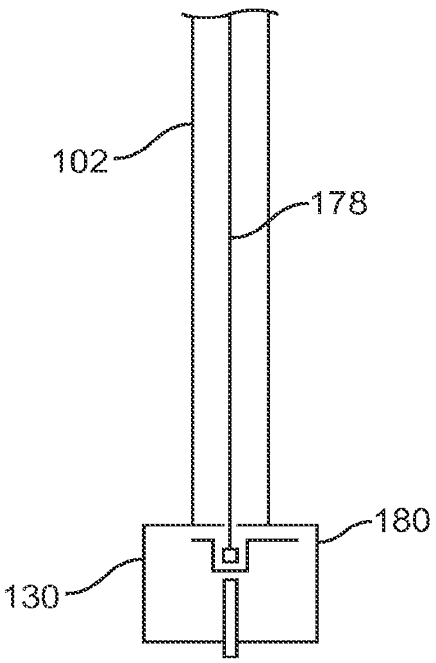

FIGS. 15A-15B shows how hydraulic and pneumatic pressure from a pressure line 178 in the shaft 102 delivered through a connector 180 can actuate the tip 130.

Figure 16:
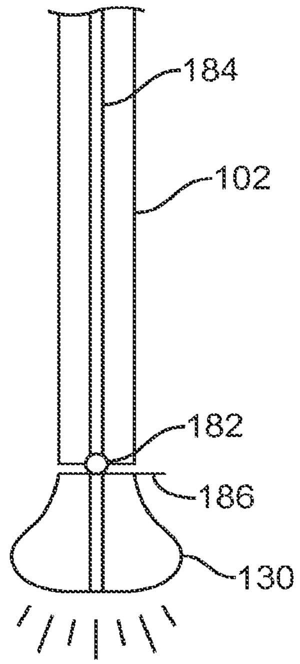
FIG. 16 shows a shaft with a mechanism to transfer heat to the tip.

FIG. 16 shows a shaft 102 with a mechanism to transfer heat to the tip 130. The shaft may also have a connector 186 with a valve 182 that will allow a heat transfer fluid to flow from a tube 184 in the shaft 102 to the tip (use of heated or cooled gas, frozen mist or liquid nitrogen, as an example). Optionally, a return path for the heat transfer fluid may also be provided in the shaft 102.

Figure 17:
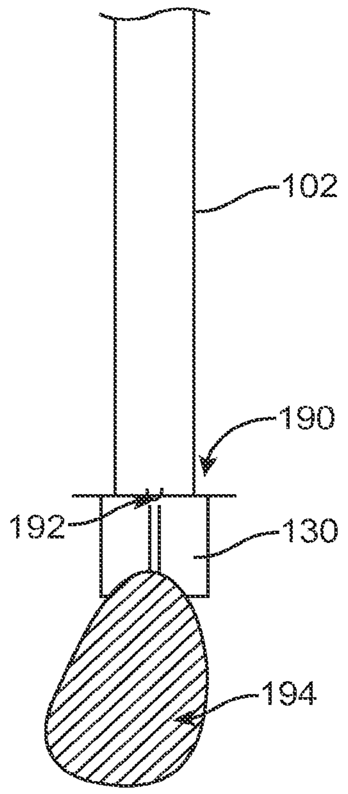
FIG. 17 shows a connector that enables flow of gas or liquid in order to inflate parts of the tip.

FIG. 17 shows a shaft 102 with a connector 190 with a valve 192 that enables flow of gas or liquid in order to inflate part 194 of the tip 130 or the entire tip. The gas/liquid could be delivered from the outside through the shaft 102 into the tip 130, through the connector 190. The inflatable part 194 may be a balloon, a tissue elevator, an inflatable actuator, etc.

Figure 18:
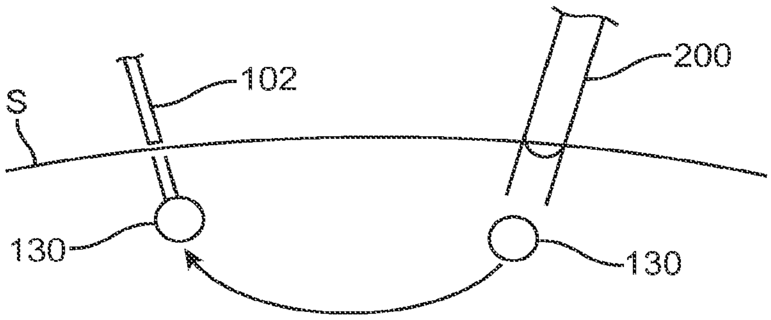
FIG. 18 shows how a big tip can be delivered through a big trocar and connected to a small trocar that is delivered in another site.

FIG. 18 shows how a big tip 130 can be delivered through a big trocar sheath 200 and connected to a small shaft 102 that is delivered in another site. The shaft 102 can be inserted through a smaller trocar sheath or directly through an opening or incision made in the skin S.

Figure 19:
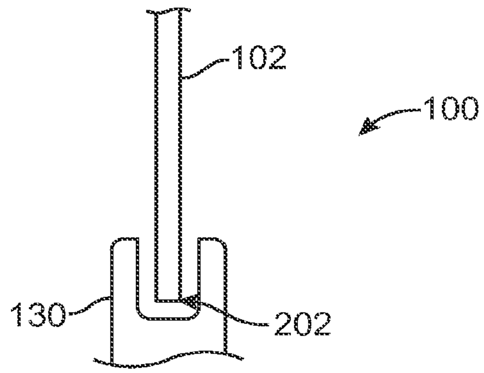
FIG. 19 illustrates a modular laparoscopy tool that uses suction to engage the working tip with the shaft.

FIG. 19 illustrates a modular laparoscopy tool 100 that uses suction 202 to engage the working tip 130 with the shaft 102. After the working tip 130 has engaged the shaft 102, a mechanical connection may optionally be made between the working tip 130 and the shaft 102. Disengagement may be accomplished by a positive pressure and/or corresponding mechanical disengagement.

Figure 20:
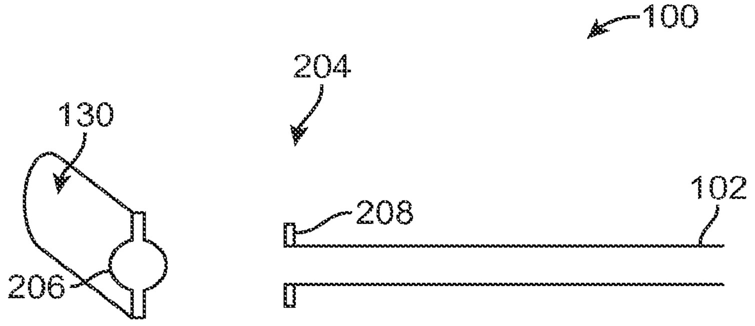
FIG. 20 illustrates an exploded view of a modular laparoscopy tool with a T-shaped connector on the distal end of the shaft.

FIG. 20 illustrates an exploded view of a modular laparoscopy tool 100 with a T-shaped or key-like connector 204 on the distal end of the shaft 102 that inserts into a cooperating slot 206 on the working tip and rotates to connect the working tip 130 to the shaft 102. Optionally, the laterally-extending pins 208 of the T-shaped connector 204 may be used for controlling and actuating the working tip 103 of the modular laparoscopy tool 100.

Figure 22:
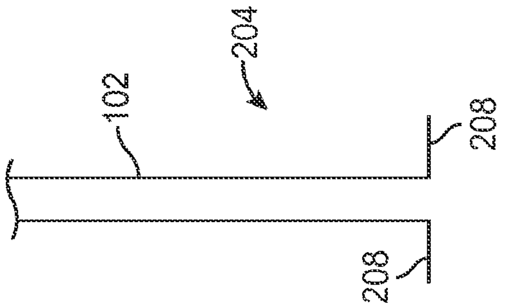
FIGS. 21-22 illustrate a T-shaped connector where the connection elements fold to give the shaft the lowest possible profile for insertion.
Figure 21:
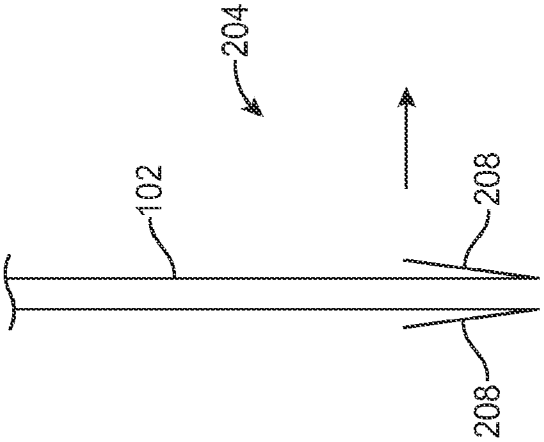

FIGS. 21-22 illustrate a variation of the T-shaped connector 204 where the connection elements 208 fold to give the shaft 102 the lowest possible profile for insertion.

Optionally, a shaft 102 may have a plurality of connection points for attaching and operating a plurality of working tips 130 with a single shaft 102.

Figure 23A:
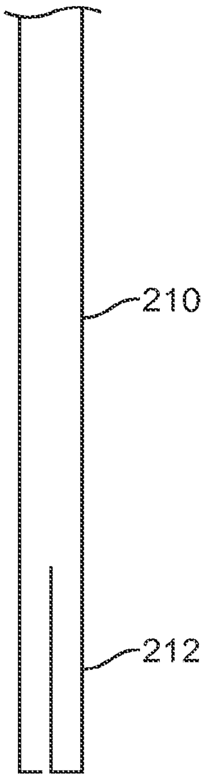
FIGS. 23A-23B illustrate a working tip delivery tool that can be used to deliver a working tip to the surgical site.
Figure 23B:
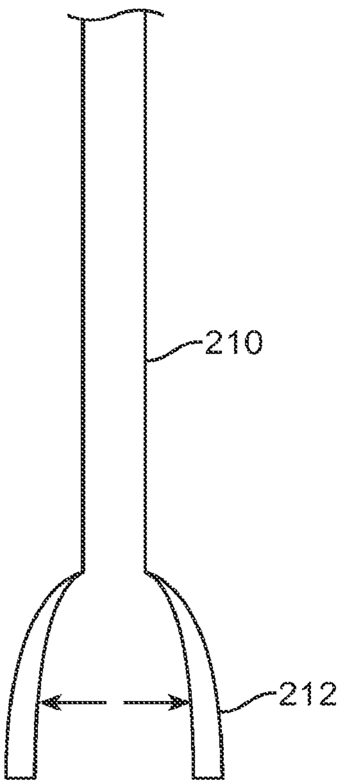

FIGS. 23A-23B illustrate a working tip delivery tool 210 that can be used to deliver a working tip to the surgical site through the lumen of the NOTES device. The delivery tool 210 has an expandable jaw 212 that closes (FIG. 23A) to hold the working tip and expands (FIG. 23B) to release the working tip after it has been attached to the shaft.

Figure 24:
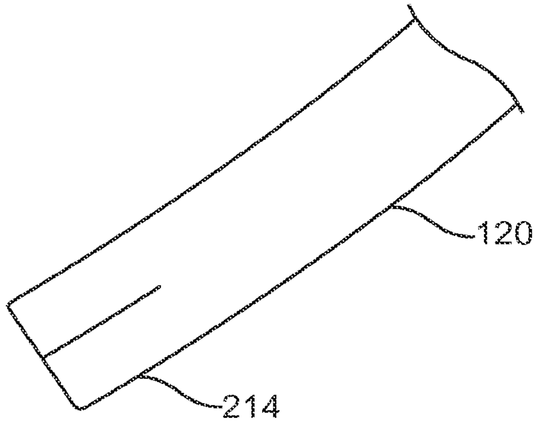
FIGS. 24-25 illustrate an overtube with an expandable jaw that turns the overtube into a working tip delivery tool.
Figure 25:
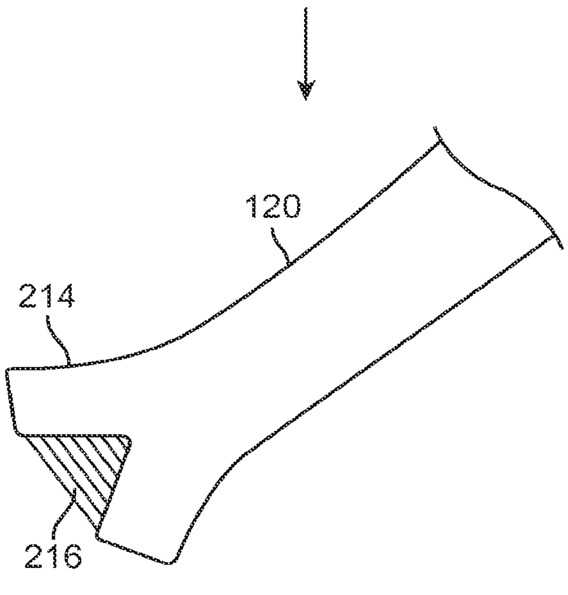

FIGS. 24-25 illustrate a NOTES overtube 120, as described above, with the additional feature of an expandable jaw 214 that turns the overtube 120 into a working tip delivery tool. The expandable jaw 214 closes to hold the working tip and expands to release the working tip after it has been attached to the shaft. Optionally, a distal portion of the overtube 120 may be made with a stretchable material 216 that allows the overtube 120 to stretch with the expandable jaw 214.

Optionally, the NOTES overtube 120 may have an anchoring mechanism at the distal end or a more proximal location, such as a ring-shaped balloon that can be inflated with gas or liquid to prevent the overtube 120 from being inadvertently withdrawn or moved from its working position in the peritoneum or thoracic cavity.

Figure 26:
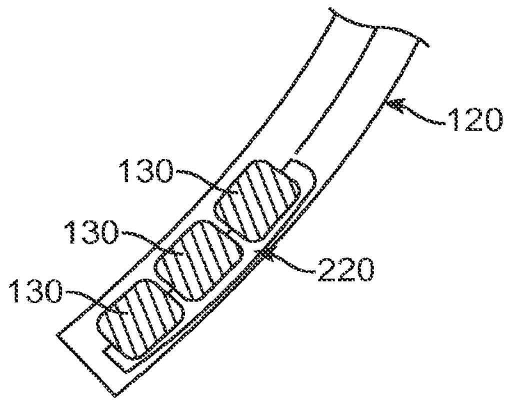
FIGS. 26-28 illustrate a working tip delivery tool that can be used to deliver multiple interchangeable working tips to the surgical site through the lumen of the NOTES device.
Figure 27:
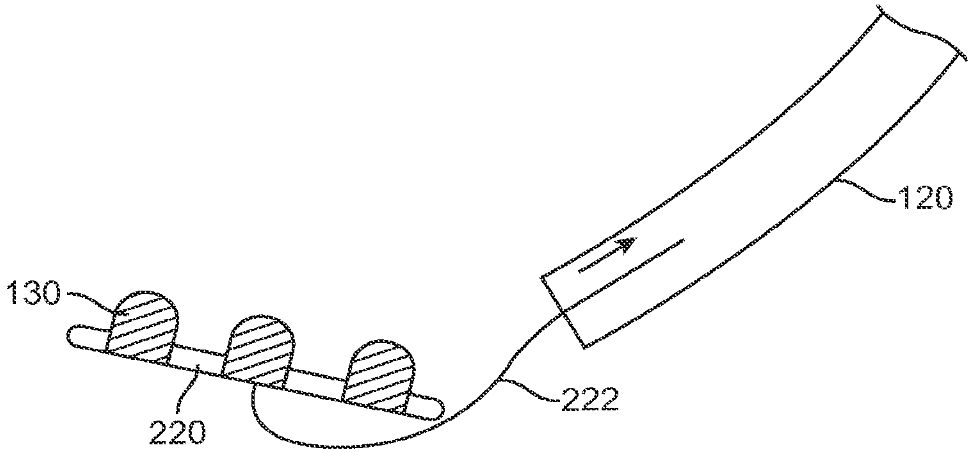
Figure 28:
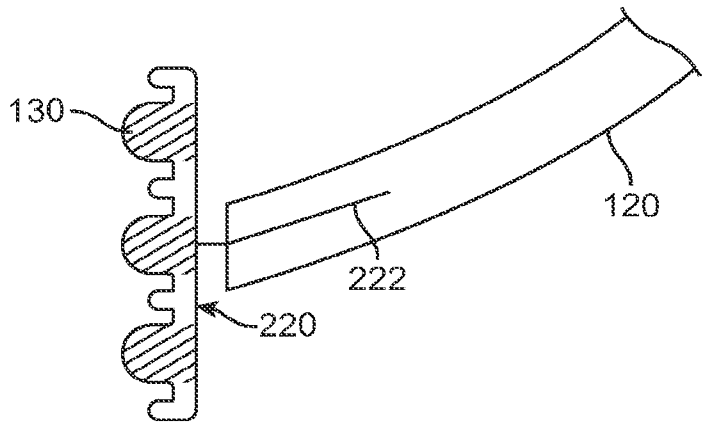

FIGS. 26-28 illustrate a working tip delivery tool 220 that can be used to deliver multiple interchangeable working tips 130 to the surgical site through the lumen of the NOTES device 120. Optionally, the delivery tool 220 will be configured to provide a "docking station" that presents the interchangeable working tips 130 in an orientation for easy attachment to the shaft of the modular laparoscopy tool. By way of example, FIG. 26 shows the delivery tool 220 being inserted through the lumen of a NOTES overtube 120. FIG. 27 shows the delivery tool 220 pushed out of the distal end of the overtube 120 within the body cavity by an elongated member 222. FIG. 28 shows the delivery tool 220 pulled back against the distal end of the overtube 120 by the elongated member 222 to present the interchangeable working tips 130 in an orientation for easy attachment to the shaft.

Figure 29:
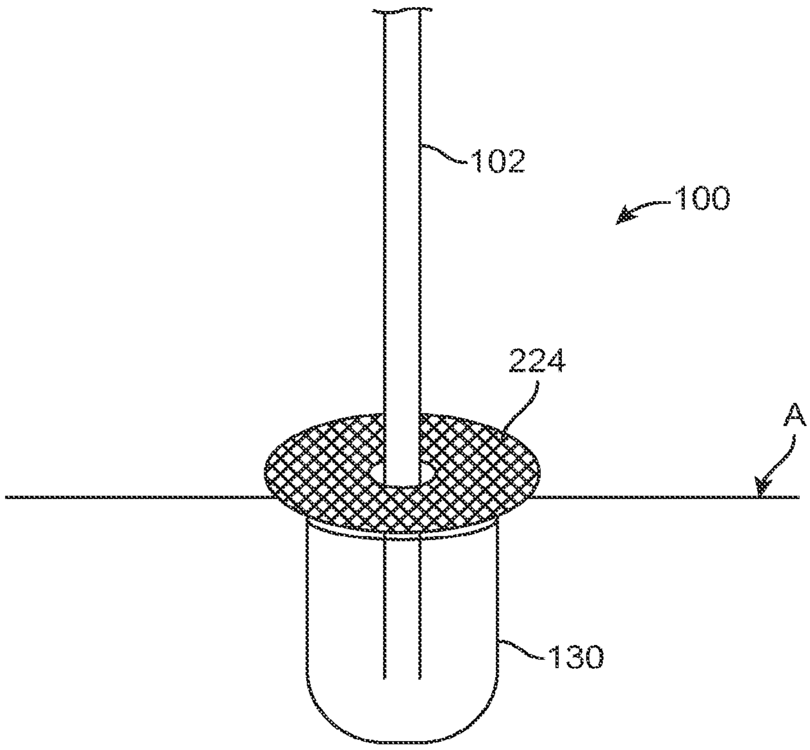
FIG. 29 shows a modular laparoscopy tool with a magnet around the shaft to attract the tip with the right alignment relative to the shaft.

FIG. 29 shows a variation of the modular laparoscopy tool 100 where a magnet 224 will be placed around the shaft 102 and will attract the tip 130 (also magnetizable) with the right alignment relative to the shaft 102. After the connection is made, the magnet 224 is optionally taken away. Alternatively, an electromagnet may be used that can be deactivated to stop attracting the tip 130 after engagement of the tip 130 with the shaft 102. Tip 130 is shown in an abdominal wall A.

FIGS. 30-35 show perspective views of a tool tip cassette 140 that can be used with the modular laparoscopy tool of the present invention. The tool tip cassette 140 is preferably sized and configured so that it can be delivered through a NOTES tool, such as the working channel of an endoscope or the lumen of an endoscope overtube, or alternatively through a laparoscopic cannula or directly through the wall of an internal organ such as the wall of the vagina. The tool tip cassette 140 has a plurality of individual tool carriers 142 that are each pivotally mounted inside of a capsule 144. Preferably, the capsules 144 are linked together by hinges 146 or other flexible connections so that it can be delivered through a NOTES tool that takes a curved or tortuous path through a body lumen to the surgical site. The hinges 146 or flexible connections also allow the tool tip cassette 140 to nestle into a compact configuration within the body cavity adjacent to the surgical site. Alternatively, if a relatively straight introduction path can be assured, the tool tip cassette 140 can be made in a rigid, straight configuration.

Figure 30:
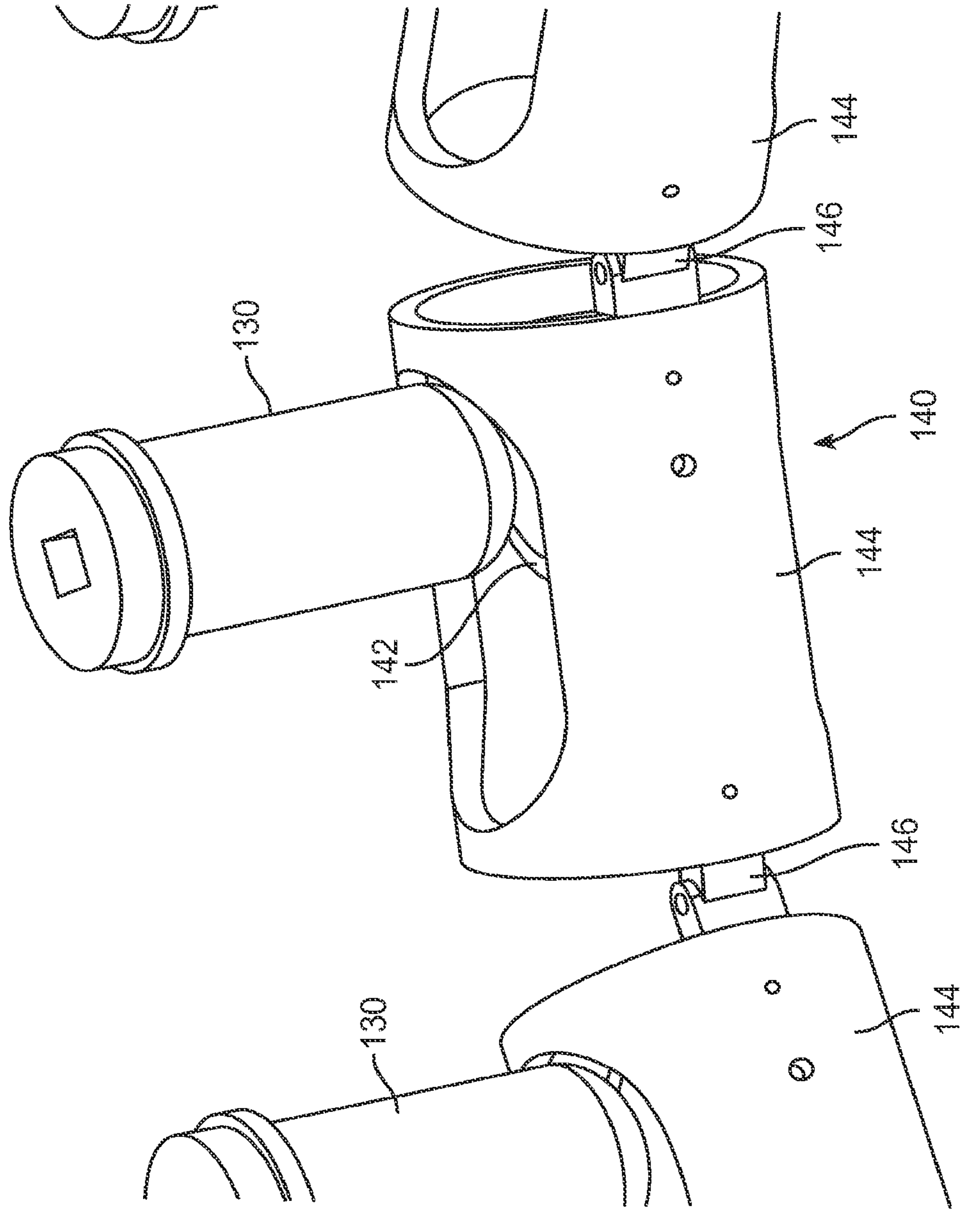
FIGS. 30-35 show perspective views of a tool tip cassette that can be used with the modular laparoscopy tool.

Each tool carrier 142 holds a working tip 130 for the modular laparoscopy tool. The working tips 130, which are shown generically, can be configured to emulate any instrument currently used in standard laparoscopy. In FIG. 30, the working tips 130 are shown being inserted into the tool carriers 142 in preparation for use. A combination of working tips 130 may be selected for a specific surgical procedure or generic tool kits with the most commonly used working tips can be provided.

Figure 31:
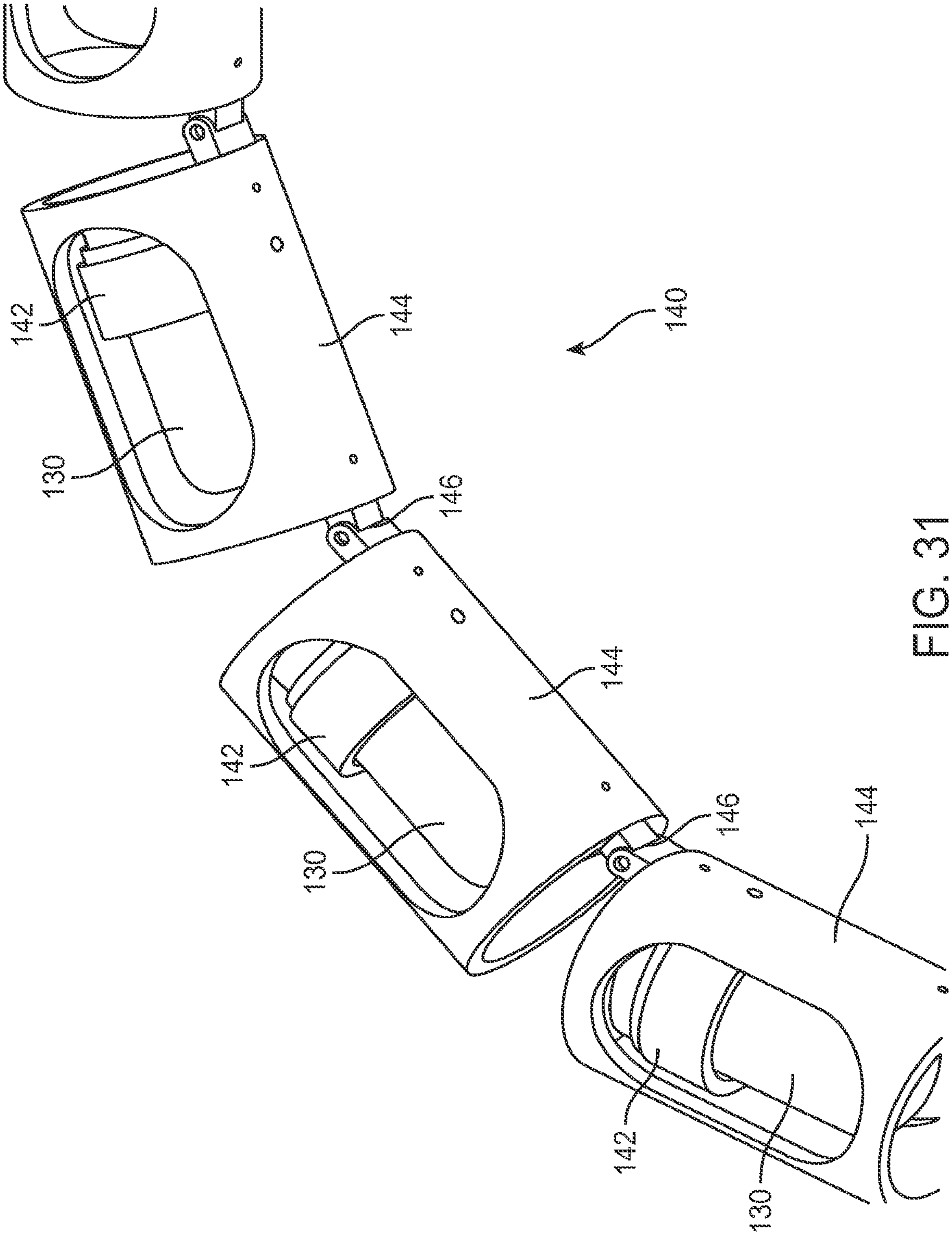

In a delivery configuration shown in FIG. 31, the tool carriers 142 are rotated so that the working tips 130 are substantially contained within the capsules 144 to minimize the delivery profile for insertion through a NOTES tool and to protect the tools during transit.

Figure 32:
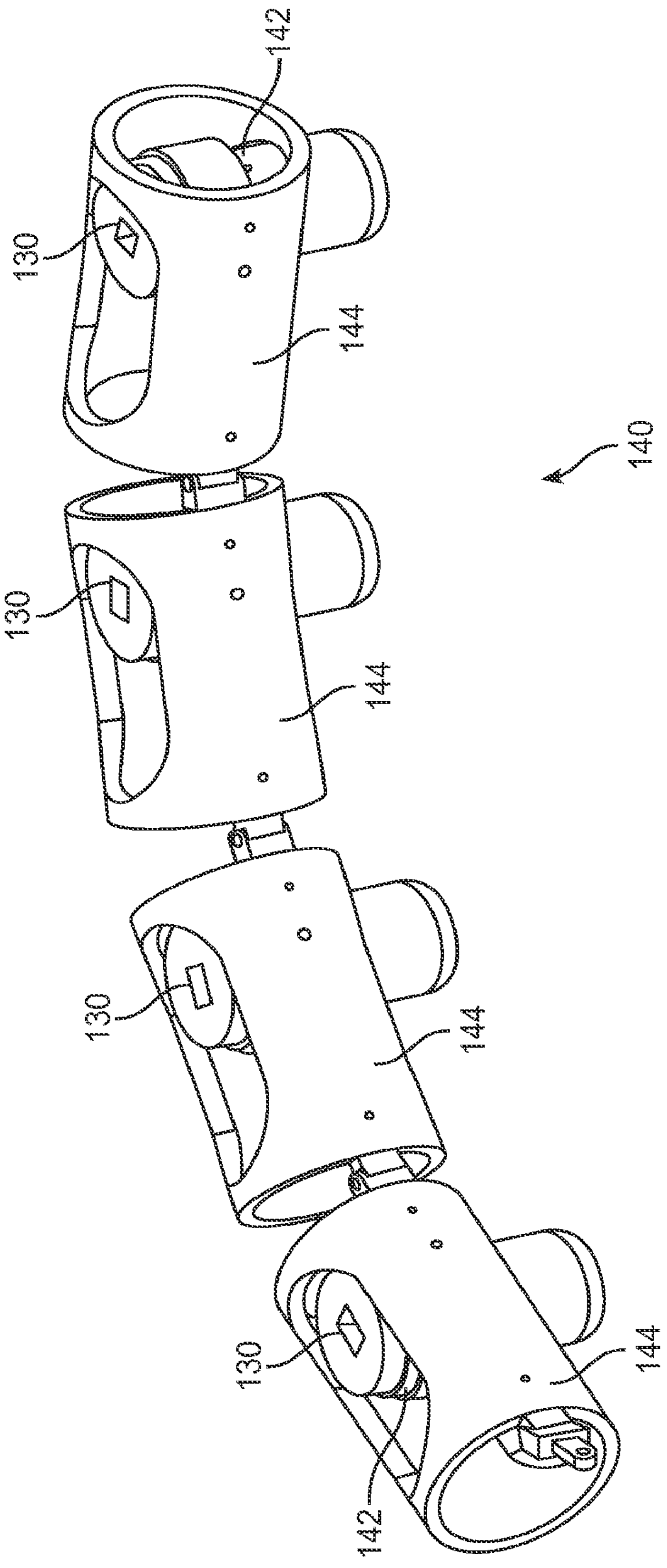

Once the tool tip cassette 140 has been inserted through a NOTES tool, the tool carriers 142 rotate to present the working tips 130 for use, as shown in FIG. 32. Optionally, the tool carriers 142 may be spring loaded so that they rotate into the presentation configuration automatically upon exiting the lumen of the NOTES tool. Alternatively, a different mechanism may be used to rotate the tool carriers 142, either one at a time or all at once. The tool tip cassette 140 is preferably configured so that the tool carriers 142 will rotate back to the delivery configuration automatically when the tool tip cassette 140 is withdrawn into the lumen of the NOTES tool. Alternatively, a mechanism selectively actuated by the operator may be used to rotate the tool carriers 142 back to the delivery configuration. Optionally, the tips will have a funnel structure around the connection point with the shaft, so that the shaft will be "taken" to the connection point accurately even if it introduced from different angles.

Figure 33:
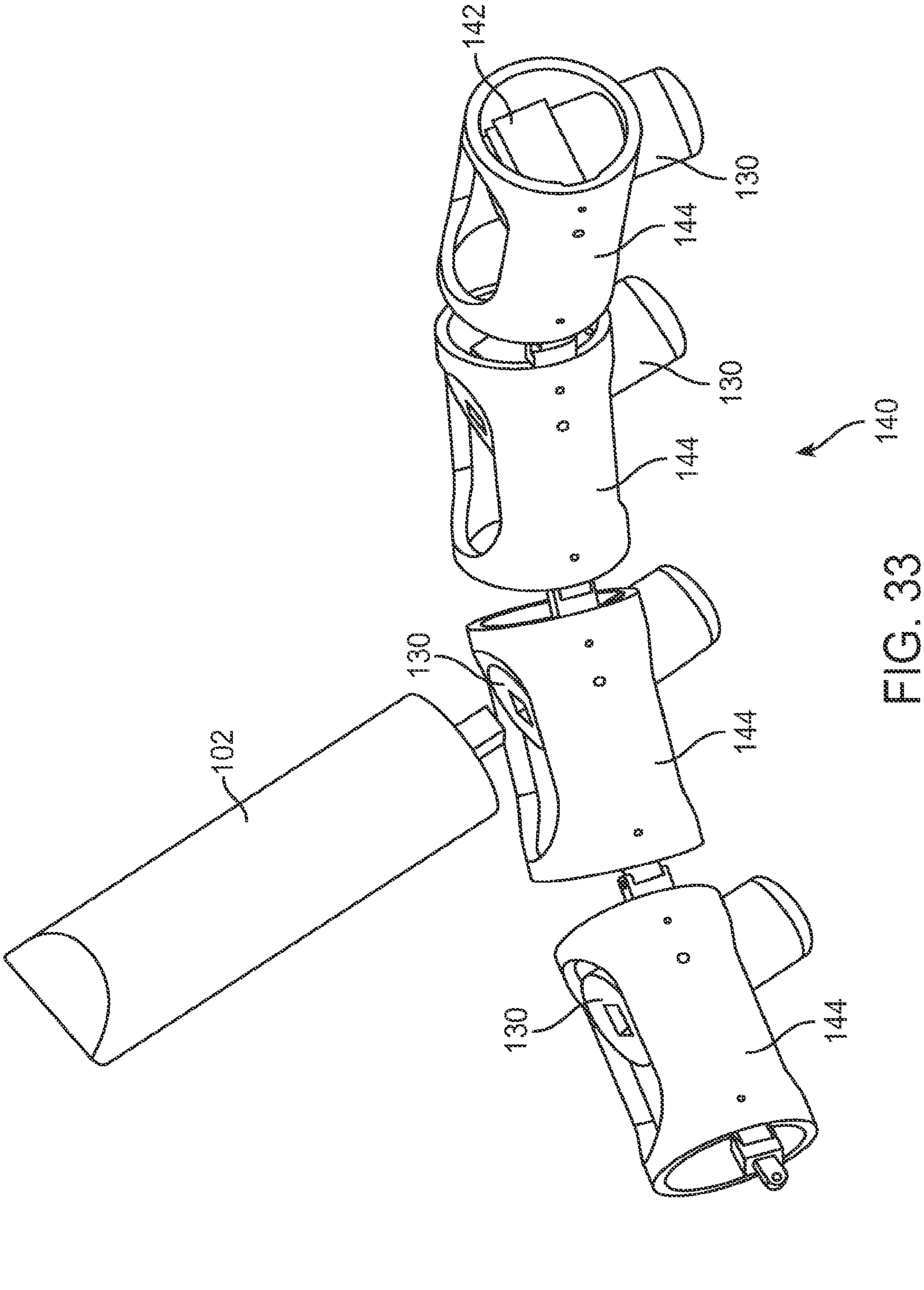
Figure 34:
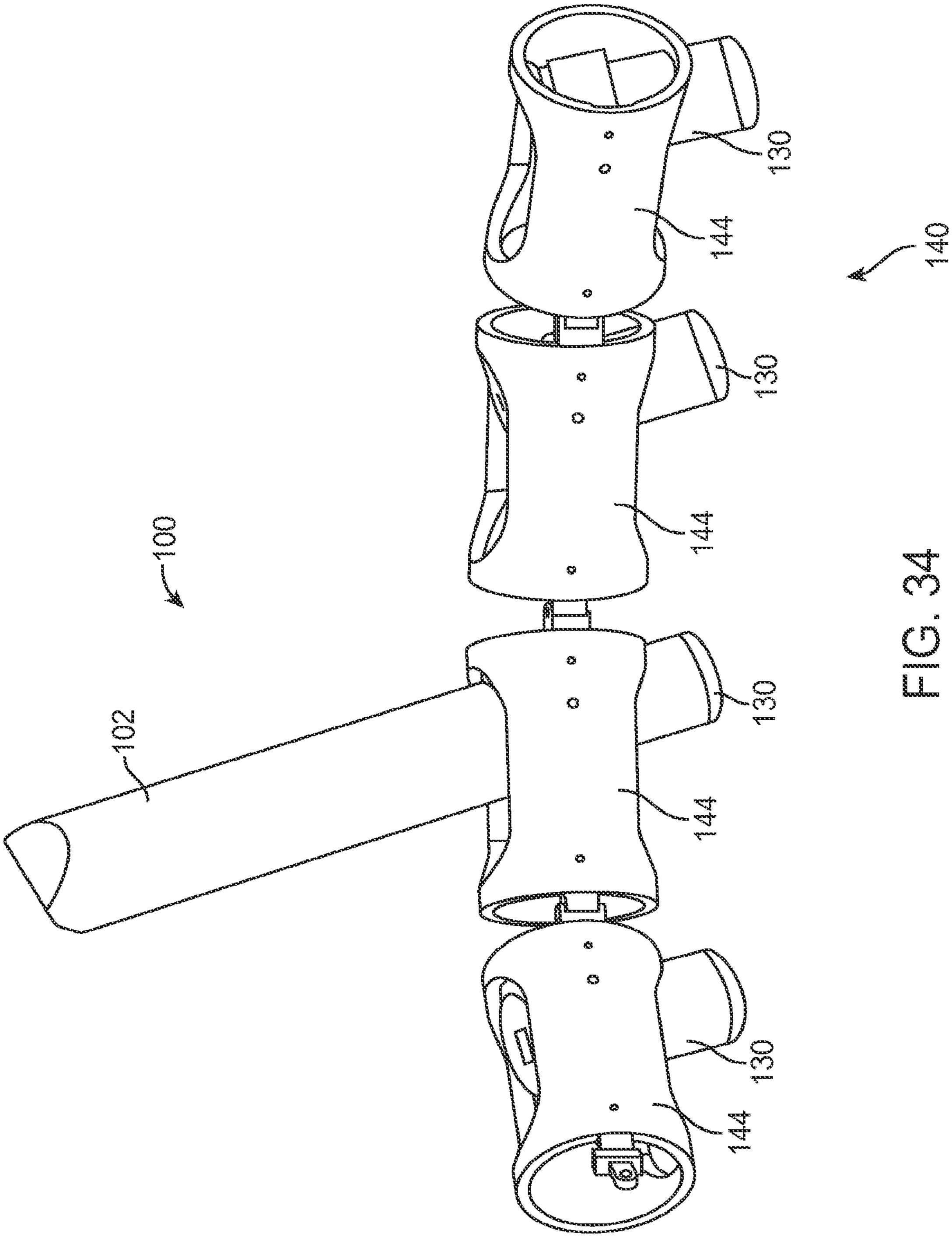
Figure 35:
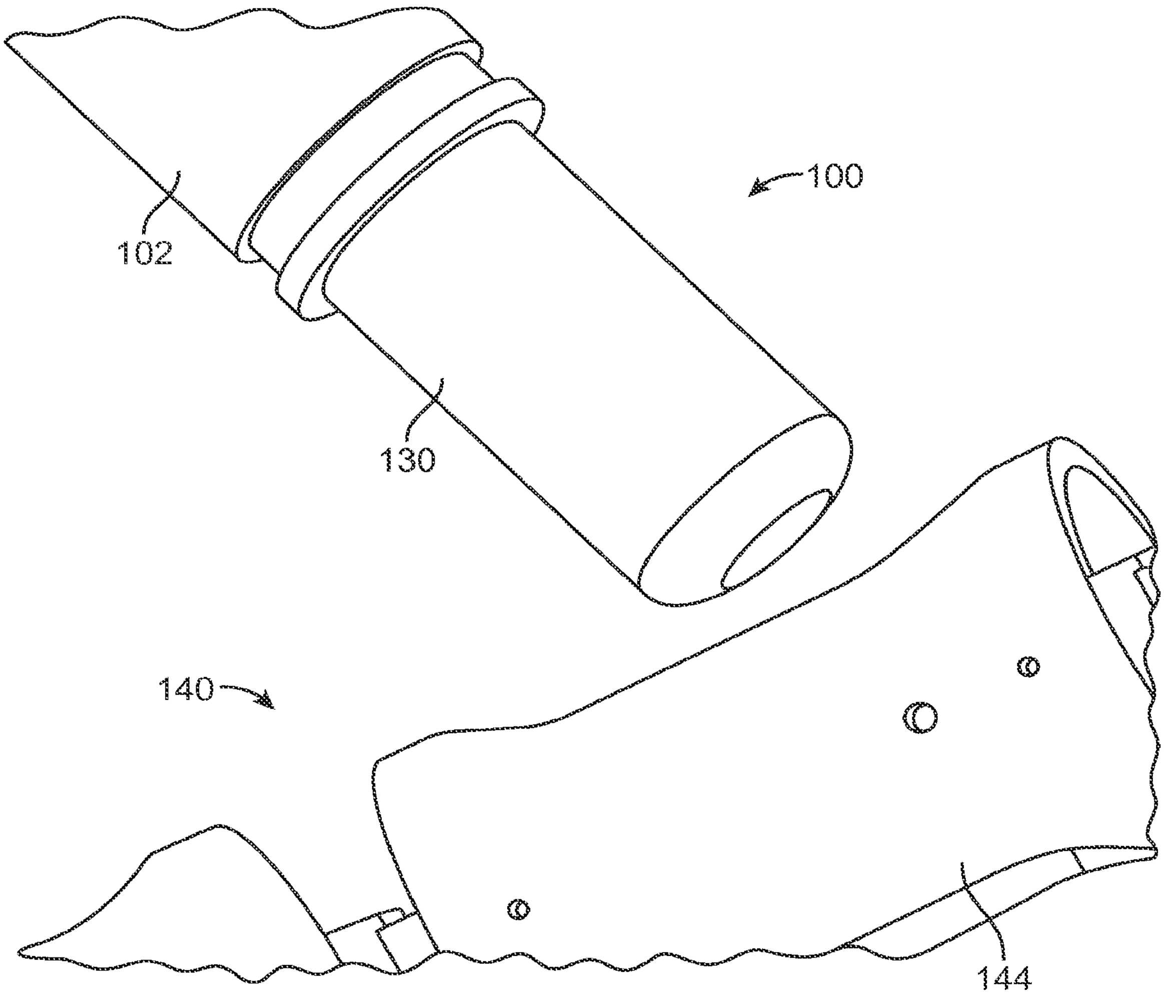

When the tool carriers 142 are in the presentation configuration, the proximal ends of the working tips 130 are presented for alignment with and attachment to the laparoscopy tool shaft 102, as shown in FIG. 33. This greatly simplifies attachment of the working tips 130 to the laparoscopy tool shaft 102. The distal end of the laparoscopy tool shaft 102 is inserted into the proximal end of the selected working tip 130, as shown in FIG. 34, and the working tip 130 is removed from the tool carrier, as shown in FIG. 35. When the surgeon is finished with a particular working tip 130, it can be returned to the tool carrier 144 and another working tip 130 can be selected. When the surgery is completed, or when the working tips 130 are no longer needed, the tool tip cassette 140 is withdrawn through the lumen of the NOTES tool.

In an alternative embodiment of the modular laparoscopy tools of the present invention, the small diameter shaft may be replaced by two, three or more even smaller diameter shafts, which are preferably 1 mm in diameter or smaller. The plurality of smaller diameter shafts will penetrate the patient's skin through separate punctures, which may be formed using a needle or the shafts themselves, and will attach to a working tip that is inserted through the lumen of a NOTES tool or other channel. Preferably, the proximal ends of the plurality of smaller diameter shafts will be attached to a single handle outside of the patient's body so that they can be manipulated as if they were a single larger-diameter shaft. Together, the combined shafts will provide as much support and control for the working tip as would a single larger-diameter shaft. The smaller diameter of the shafts will assure that there is even less trauma to the patient from insertion of the tool. Optionally, relative motion of the plurality of shafts (translation and/or rotation) can be used to provide control actuation for the working tip.

In one optional embodiment of the modular laparoscopy tools of the present invention, the attachment mechanism for connecting the working tip to the shaft (or shafts) is constructed so that, when the shaft is pushed a first time into the tip, it attaches the shaft to the tip, and, when the shaft is pushed a second time, it detaches the shaft from the tip. The attachment mechanism may be configured to require a force for attachment and detachment that is above a threshold for normal surgical manipulations of the tool. The attachment mechanism may be located in the shaft or, more preferably, in the tip.

Many different tools are currently used in laparoscopic surgery, any of which can be readily adapted for use with the modular laparoscopy tools of the present invention. A fairly comprehensive list of instruments currently used in laparoscopic surgery is provided below in Table 1. Any of these instruments can be used as the basis for a working tip configured for attachment to the shaft of the modular laparoscopy tool. Other surgical tools, as well as instruments developed in the future, can also be adapted for use with the modular laparoscopy tools of the present invention.

Some specific examples include a surgical tool tip that includes a suction and/or irrigation tube that extends through a natural body orifice and/or the internal lumen of the NOTES delivery tube to the surgical site. The distal end of the suction/irrigation tube can be held by or attached to a modular laparoscopy tool to control the location, direction and flow rate of suction and/or irrigation through the tube. One or more illumination devices, such as LED, incandescent or fluorescent lights, or optical fibers, can be delivered through the NOTES delivery tube and positioned at various places within or around the surgical site for effective illumination using a modular laparoscopy tool. One or more cameras, video cameras or other imaging devices can be delivered through the NOTES delivery tube and positioned at various places within or around the surgical site for effective imaging of the surgical site using a modular laparoscopy tool. The illumination and/or imaging devices can be attached to the walls of the body cavity or set up on legs or other supports within the body cavity. The illumination and/or imaging devices can include magnets allowing them to be aimed using a magnet external to the patient's body. A working tip with a grinder or morcellator can be used to reduce the size of an excised organ or tissue for easy removal through the NOTES tool or a laparoscopic tool. A working tip can have electrodes for ablation or electrophysiology measurements.

TABLE 1

Instruments used in laparoscopy

| Category | Examples |
|---|---|
| Needle Drivers | |
| Scissors | Curved Scissors<br>Round Tip Scissors<br>Potts Scissors |
| Scalpels | |
| Graspers | Cadiere Forceps<br>Tenaculum Forceps<br>Cobra Grasper<br>DeBakey Forceps<br>Double Fenestrated Grasper<br>Resano Forceps<br>Thoracic Grasper<br>Grasping Retractor |
| Monopolar Cautery Instruments | Monopolar Curved Scissors<br>Cautery Hook<br>Cautery Spatula |
| Bipolar Cautery Instruments | Maryland Bipolar Forceps<br>PK Dissecting Forceps (Gyrus/ACMI/Olympus)<br>Fenestrated Bipolar Forceps<br>LigaSure (ValleyLab/Covidien) |
| Ultrasonic Energy Instruments | Harmonic Curved Shears (Ethicon) |
| Closure/Clip Appliers | Hem-o-lok Clip Applier (Weck)<br>EndoClip (Autosuture/Covidien)<br>EndoStitch (Autosuture/Covidien) |
| Anastomosis Devices | EEA (End-to-End Anastomosis/circular stapler)<br>GIA (Gastrointestinal Anastomosis/linear stapler) |
| Specialty/Misc Instruments | Atrial Retractor<br>Valve Hook<br>Pericardial dissector<br>Dual Blade Retractor<br>Mesh Tacking Device |
| Suction/Irrigation Instrument | |
| Specimen Retrieval Instrument (bag) | |
| Implant Delivery Device/system | |
| Rigid endoscope (and camera) | |

Various robotic surgical systems have been developed that are usable for robotic assisted laparoscopic surgery. Examples of such robotic surgical systems include the DA VINCI Surgical System, available from Intuitive Surgical, Inc. and the ZEUS Robotic Surgical System previously available from Computer Motion Inc. All of the published patents and patent applications of these two companies are hereby incorporated by reference. While these systems represent a tremendous technological advance in the area of robotic assisted surgery, they suffer from some of the same drawbacks as standard laparoscopic surgery. In particular, robotic assisted laparoscopic surgery still requires 1-2 cm incisions for insertion of the instruments, as does standard laparoscopic surgery. This is a great improvement over open surgery, but it still requires some convalescence time for the patients and carries some risk of herniation at the incision site. Further miniaturization of laparoscopic tools has been attempted, but the resulting tools proved to be too fragile and limited in their use. It would be beneficial therefore to the patients as well as the surgeons to provide a robotic surgical system that minimizes the invasiveness of the surgery while simultaneously improving the effectiveness of the robotic laparoscopic tools used. This can be accomplished by utilizing modular robotic laparoscopy tools with very thin shafts to minimize the puncture size needed to insert the tools through the abdominal wall and using an endoscope working channel or an overtube inserted using NOTES techniques as a conduit to deliver larger diameter end effectors of the modular robotic laparoscopy tools that will attach to the shaft or shafts inside the body. Alternatively, a single larger laparoscopic cannula can be used to deliver the larger diameter end effectors of the modular robotic laparoscopy tools to the surgical site. Optionally, the endoscope or NOTES tool and/or the end effector delivery system may also be robotically controlled.

Figure 36:
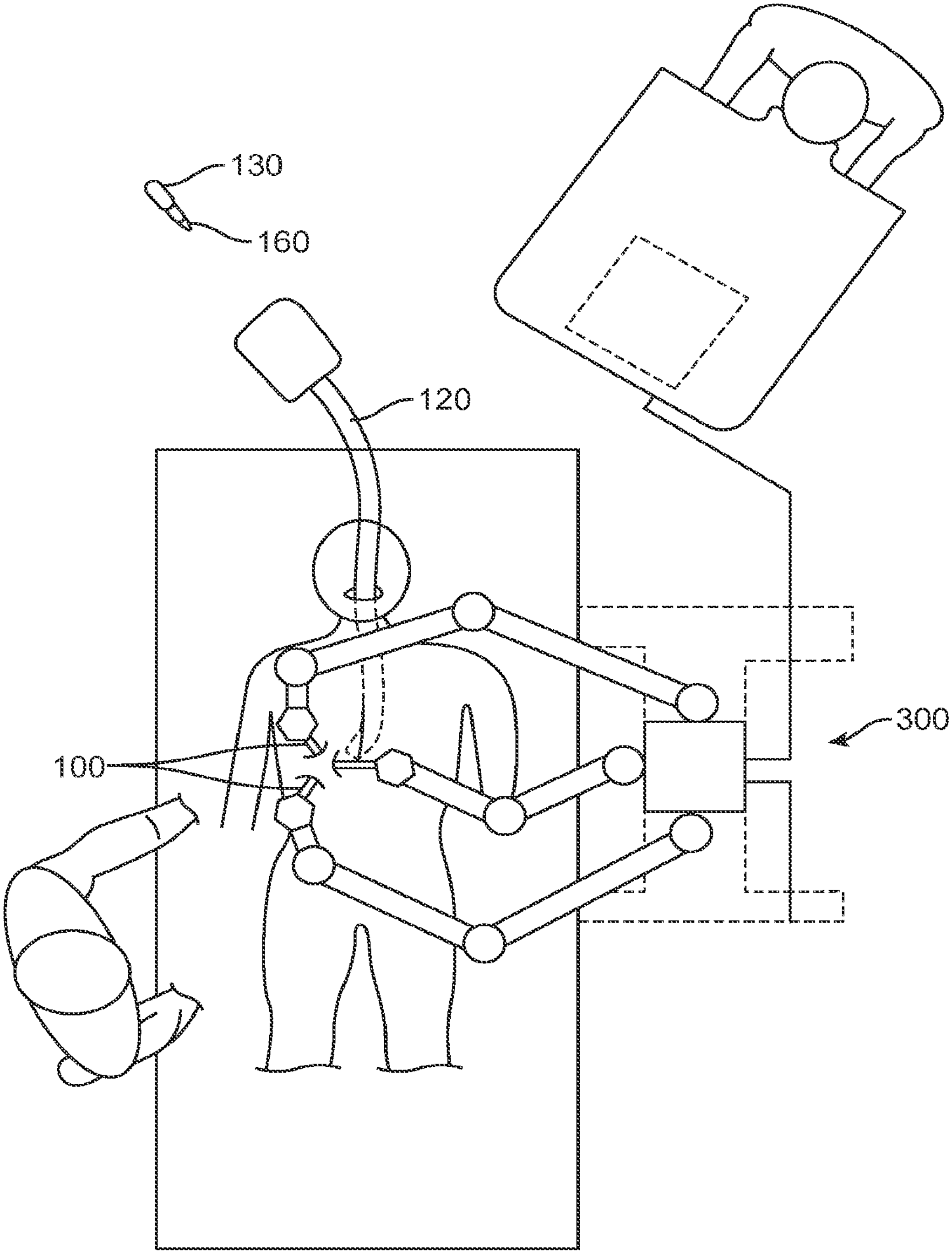
FIG. 36 illustrates apparatus for robotic assisted hybrid endoscopic and laparoscopic surgery.

FIG. 36 illustrates an example of the improved apparatus and methods of the present invention adapted for robotic assisted hybrid endoscopic and laparoscopic surgery. One or more modular robotic laparoscopic tools 100 are operated using a robotic surgical system 300. The working tips 130, with robotically operated end effectors 160, of the modular robotic laparoscopy tools are preferably delivered to the surgical site through an endoscope working channel or an overtube 120 inserted through a natural body orifice using NOTES techniques. Optionally, the overtube 120 may be inserted into the patient's body through a natural orifice and advanced to the surgical site mounted concentrically over a flexible endoscope. The surgical site may be located in the thoracic or abdominal cavity or within an organ of the patient's body. Once the overtube 120 is in position at the surgical site, the flexible endoscope is preferably withdrawn. Alternatively, a single larger laparoscopic cannula can be used to deliver the end effectors to the surgical site. Optionally, the endoscope or overtube 120 may also be used in other ways to assist in the surgery using NOTES techniques, for example for evacuation of tissue or organs that were retrieved during the surgery.

Figure 37:
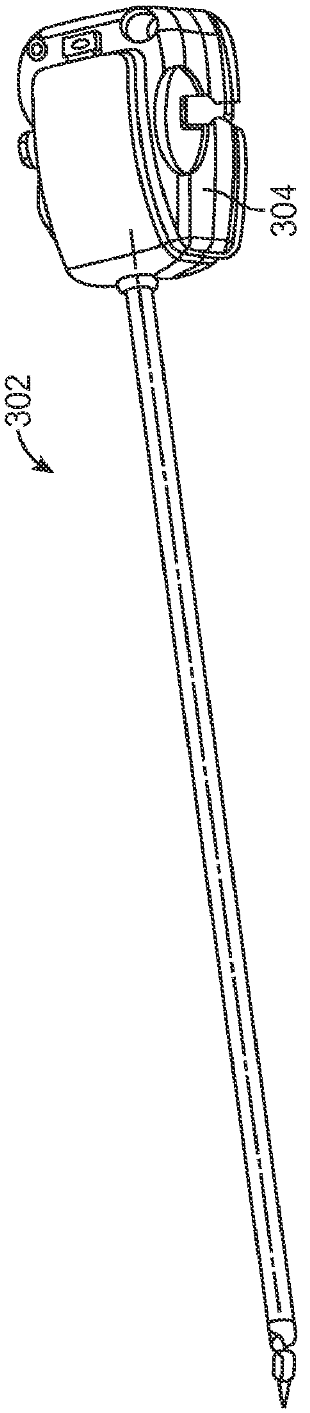
FIG. 37 (PRIOR ART)
FIG. 37 illustrates a prior art robotic end effector for laparoscopic surgery.

FIG. 37 illustrates an example of a prior art robotic end effector 302 for laparoscopic surgery. In use, the proximal end 304 of the end effector 302 is attached to a robotic arm of a robotic surgical system and the end effector 302 is operated by the robotic surgical system 300.

Figure 38:
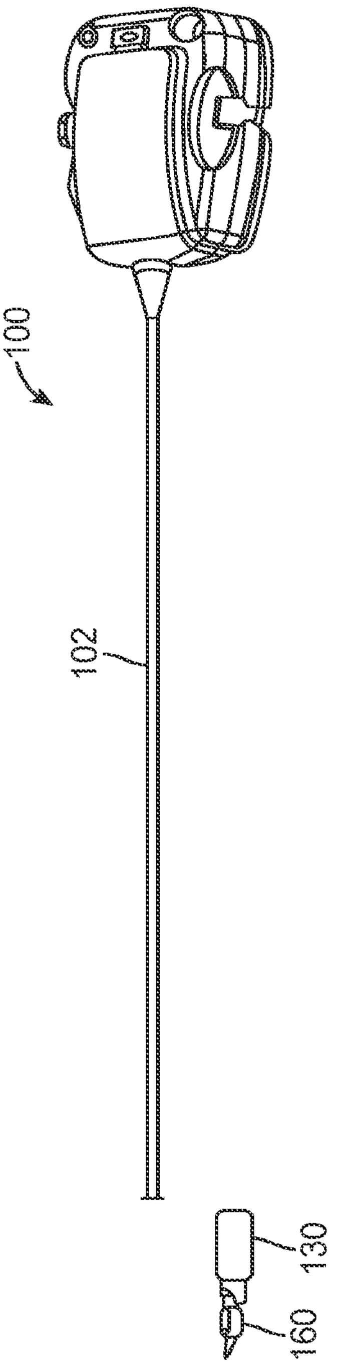
FIGS. 38-39 illustrate a modular robotic laparoscopic tool adapted for use in the improved apparatus and methods for robotic assisted hybrid endoscopic and laparoscopic surgery of the present invention.
Figure 39:
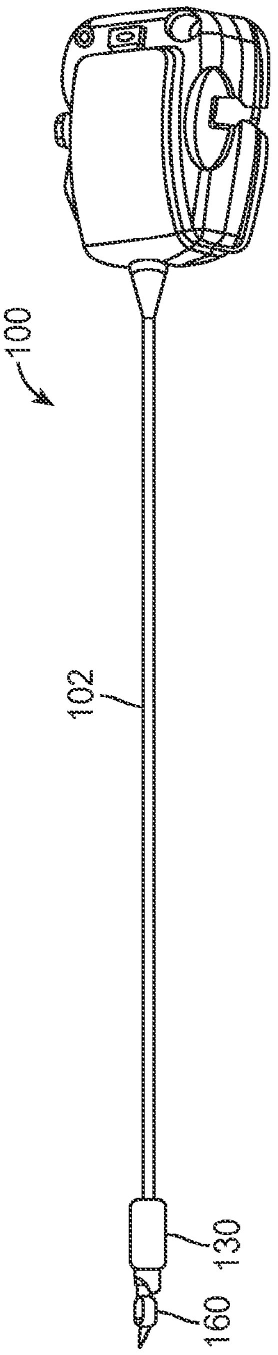

FIGS. 38-39 illustrate an example of a modular robotic laparoscopic tool 100 adapted for use in the improved apparatus and methods for robotic assisted hybrid endoscopic and laparoscopic surgery of the present invention. The modular robotic laparoscopic tool 100 has an end effector 160 component that is configured as a detachable working tip 130 with means for connection to a modular robotic laparoscopic tool shaft 102. Preferably, the shaft of the tool has a diameter of approximately 1-5 mm. The detachable working tip 130 with the end effector 160, which may have a significantly larger diameter than the shaft 102, is preferably delivered to the surgical site through an endoscope working channel or an overtube inserted through a natural body orifice using NOTES techniques and attached to the distal end of the shaft 102 inside of the patient's body. Any of the modular laparoscopic tools described herein can be adapted to operate as a robotic end effector.

The end effector 160 on the detachable working tip 130 may be operated directly though the shaft 102 of the modular robotic laparoscopic tool 100 by the robotic surgical system similarly to the prior art end effector 302 described above. For example, pull wires, pushrods, rotating shafts and/or pneumatic or hydraulic channels in the shaft 102 may be used to operate the end effector 160. Alternatively, the end effector 160 may be operated remotely in a master/slave relationship with the robotic surgical system or a separate robotic controller. Motors or other actuators may be included in the detachable working tip 130. Control signals may be sent to the end effector 160 through the shaft 102, or through an umbilical cable that extends though the NOTES access channel or through or alongside the shaft 102. Control signals may be sent to the end effector using wireless technology, for example using radio, optical, magnetic, sonic and/or ultrasonic control signals. Power to operate the end effector 160 may be supplied through the device shaft 102, through an umbilical cable or from a battery or other power source on board the detachable working tip 130.

In this invention, a robotically controlled shaft 102 whose position and movement in space is controlled by a computer via a master slave system, will be connected to a tip 130 that is delivered in a separate or different port or conduit. After the connection, the computer may also control the actuation of the tip 130 which, as long as it is connected to the shaft 102, may move in space with the shaft 102. The operator may work on a separate working station where he or she will move a master unit and the unit that will control the shaft's position and motion will be controlled by a robotic slave unit. The slave unit may also control the spacial position of the tip 130 as well as actuation of the active part of the tip.

Unlike a traditional robotic tool where the shaft is always connected to the tip, in this invention the shaft 102 is not always connected to the tip 130.

In one option, the tip 130 may include actuation means inside, like motors, and the master unit's activity will be translated to electric signals that will actuate the tip to do what the operator is doing in the working station.

The robotic shaft 102 may have one or more bendable parts so that the shaft's distal part can be directed to the side and in such a way direct the tip in a specific direction after the connection of the tip to the shaft.

The following describes optional features that may be utilized in the implementation of the modular laparoscopy tools of the present invention.

Optionally, the modular laparoscopic tool 100 may include an indicator light or type of other indicator to show when the working tip 130 has been correctly connected to the tool shaft 102.

The NOTES instrument can be a flexible endoscope. Each laparoscopic instrument consists of a "shaft" which can mate to or release a "tip" or tool at the distal end. The scope may or may not be provided with an "overtube". If the scope is provided with an overtube then, after the scope has been properly positioned near the surgical site, the scope can be withdrawn, while the overtube is left in place, allowing use of the full working diameter of the overtube to deliver tips too large to pass through conventional scope working-channels. The scope or overtube may or may not be provided at its distal (working) end with a "docking station"—which may consist of nothing more than a ring or latch—to catch the tip as it is delivered through a working-channel or overtube. A tip can be visualized as contained within a (roughly) cylindrical volume with two "ends". The distal, or working end, or the tip is the part in closest proximity to the tissue during a surgical procedure. The distal end of the tip is oriented toward the distal (working) end of the scope during passage along the scope working channel. The proximal (mating) end of the tip will typically have some type of means to releasably mate with the laparoscope shaft and in many cases will also have means to transmit mechanical, electrical, RF, pneumatic, hydraulic, or optical energy required to actuate the tip or to perform electrocautery and/or transmit or return signals conveying information such as (but not restricted to): (i) an image of the surgical site, (ii) haptic information from a force-torque sensor integrated into the tip, (iii) signals to control the state of the tip, such as whether grasper position is locked, to actuate any mechanism required to engage or disengage the tip from the docking station or shaft.

The rationale behind Laparoscopic surgical techniques is to avoid the trauma associated with open surgery. Rigid shafts are used to manipulate micro-surgical instruments inserted through very small incisions. Because the shafts are rigid the surgeon has precise control over their movement and is also provided haptic sense or "feel" of the mechanical characteristics of the tissue. Incision lengths of 5-10 mm, however, do not allow the use of many important surgical tools, which are simply too big to pass through such a small incision.

One response to this has been to introduce "Natural-Orifice Transluminal Endoscopic Surgery" or NOTES. NOTES procedures utilize a surgical robot or "scope" derived from endoscope technology, to deliver surgical tools to the site via one of the "natural orifices" of the human body: trachea, esophagus, anus, vagina, or umbilical closure. The surgeon controls such an instrument via a joystick-type interface while observing a video image provided by a small camera built into the distal end of the scope. Tools are passed through one or two "working channels". While NOTES allows the use of larger surgical tools, the scopes are insufficiently rigid to hold position against typical reaction forces and torques generated by surgery, no haptic sensory feedback is available to the surgeon, and the control interface is confusing to those skilled in laparoscopic procedure.

The present invention proposes a better, hybrid, approach, incorporating the following elements: (i) a laparoscope shaft which can engage and disengage from any tool, making it possible to insert the shaft alone, sans tool, through a very small incision, (ii) a set of modular tools, each of which can pass through a NOTES-scope working channel or overtube as well as mate with the laparoscope shaft, (iii) various means of providing energy to the tool to perform the task for which it is intended and (iv) various means to exchange control signals or information, such as video information or data from haptic sensors, with the tool.

A NOTES endoscope is inserted prior to the surgery or in the first stage of the surgery and manipulated so that the distal end of the scope is in proximity to the intended surgical target site. Independently of the scope, incisions for the laparoscopic shafts are made and the shafts inserted. The first tool is selected and delivered, mating-end first, to the distal end of the scope. The surgeon manipulates the shaft tip into contact and mates shaft and tool, the tool is released from the scope and brought to the surgical site, the current step in the surgical procedure is performed, the tool is returned to the scope, the tool is withdrawn from the body via the scope working channels, the tool required for the next step in the surgical procedure is selected and delivered to the distal end of the scope to repeat the process.

In some cases it may be desirable to use a scope fitted with an "overtube". After the tube is inserted and manipulated to reach the surgical site, the scope alone may be withdrawn, leaving the overtube in place. In this case, tools can be inserted and removed via the (larger-diameter) overtube.

A wide variety of modular tools are possible: Staplers are one of several tools too large to pass through a laparoscopic incision which can, however, pass through a working channel or overtube, and can therefore be used with the proposed approach.

Some additional possibilities suggested by the modular MIS concept:

In the present invention, the scope or the tube serves two primary functions of: (i) delivery of the tip to the shaft and (ii) retrieval and/or exchange of the tip at the completion of the surgical phase requiring this tip. In addition, the scope, otherwise idle during the surgical procedure after delivery of tip to shaft, may also serve to hold a fixture to facilitate some surgical step, such as knot tying or suturing. See, for example, the publication from Dartmouth entitled "Knot tying with single piece fixtures". Such a fixture might be permanently inter-grated into the docking-station to be available at all times during surgery.

Use of scope to support a fixture: After transfer of the tip tool to the laparoscope shaft the scope is free to perform other functions during surgery. For example, one or more fixtures can be provided at the distal end of the scope, such as a fixture to assist with knot tying or other procedures.

The scope can also be used to carry one or more fixtures to assist with a surgical procedure or to make possible a procedure which would otherwise be impossible using only two shaft-mounted tools, such as knot-tying. Such fixtures can be permanently attached to the scope or (alternatively) might be made "tool-like", so that the fixture could pass through a scope working channel or the overtube to attach and be retained at the end of the scope only for the duration of the particular surgical step for which it is needed. Such a fixture can also carry movable mechanical elements requiring any of the various type of actuation considered above. Since the fixture will remain attached to the scope during the procedure, it is not necessary, in this case, to provide disengageable connectors at the fixture itself.

Use of scope to carry an additional tool. After a tip has been passed to the shaft, a new tool can be extended to the scope distal end to participate in the surgical procedure or act as a "third-hand". In some cases this may allow use of only a single shaft (and single incision) for the procedure.

Idle Scope can Hold a Second Tool

An oft-stated limitation of NOTES is that the two working channels provided by the scope are separated by only a small distance, hindering simultaneous use of two instruments 1 Perhaps it should be mentioned that, in addition to serving a "third hand" to hold a fixture or some other device in proximity to the surgical site, the scope can also serve to hold a second tool, for example, a clamp to fix tissue in place while the surgeon performs a procedure requiring fine motor control using a tool transferred to one or the other laparoscopic shafts.

Coordinated activity of scope and laparoscopic tool: In cases where the scope is not idle, and participates in one of the above ways during surgery, means may be provided to sense the position and orientation of the shafts and a software component provided to control the scope in such as way that motion of the scope automatically follows surgeon-controlled motion of the shafts. Different scope motions will be required for different scope tasks. For example, if the scope is providing a stereo view of the surgical site, the scope may have to automatically orient to image one or both shaft tips, and motion compensation software may be incorporated to compensate for patient motion or vibration. If the scope is acting as a "third hand", software to "actively stiffen" the scope may be required.

To simplify the "docking" maneuvers required to orient and align tip to shaft prior to attachment or detachment of the tip to shaft, a "software component" may be utilized to provide automatic control of the scope while passively monitoring the position and orientation of the laparoscopic shafts as they are manipulated by the surgeon. In case simultaneous use of scope- and shaft-mounted tools is used, such software could also be used to automate scope positioning or to "stiffen" the scope via active feedback.

It is also possible to transmit energy and/or information to the tool via an "umbilical" cord which remains connected to the scope during the surgical procedure and which may, for example, run down the second working channel to attach to devices located outside the patient's body. Use of an umbilical connection of this type is clearly feasible when the tool is delivered via an overtube. Use of an umbilical will fully or partially eliminate the need for any additional attachment or connectors between shaft and tool, other than the mechanical mating connection.

One method of delivering tip to the end of a scope working channel is to thread a cable attached to the tip through the scope's second working channel and then "pull" the tip to the end of the primary channel using the thread or cable. This raises the possibility that cables needed to carry energy and signals required to actuate and control the tip would also thread through the second working channel. In this case, after the shaft has attached to the tip, and the tip has been released from the docking-station, an "umbilical" consisting of these cables would continue to connect tip and scope during surgical use of the tool. In this case, it would not be necessary to provide any additional connection between shaft and tip, beyond that required to attach and retain the tip.

It is also possible to transmit energy and/or information to the tool via an "umbilical" cord which remains connected to the scope during the surgical procedure and which may, for example, run down the second working channel to attach to devices located outside the patient's body. Use of an umbilical connection of this type is clearly feasible when the tool is delivered via an overtube. Use of an umbilical will fully or partially eliminate the need for any additional attachment or connectors between shaft and tool, other than the mechanical mating connection.

Umbilical: electrical and hydraulic cables required to transmit control or video signals and/or power to actuate the tip tools can be provided via an umbilical cable, which remains attached to the scope during the surgical procedure. The shaft need only carry the means to couple to the tip and retain it during the surgical procedure. The umbilical cable will pass down one of the two working channels of the scope (here identified as the secondary channel). When the tip is retrieved via the primary working channel, any connectors at the proximal end of the umbilical cable will be detached to allow the umbilical cable to be pulled back through the primary working channel behind the tip.

Navigational aid—In some cases it may be desirable to be able to track the location of shaft-mounted tips within the body, perhaps to reference the 3D position of the tip with respect to the 2D image provided by the scope camera, or in reference to the scope itself. In this case, the scope might be provided with short range transducers—for example, ultrasonic ranging transducers—which could be used to determine the location of a shaft-mounted tip relative to the scope. A software component, monitoring the actual position of the scope, via Ascension-type magnetic encoders, scope "shape-sensors" or other means, could the calculate, report and display the true position of the tip within the body.

A scope may be fitted with magnetic position and orientation sensors, allowing the position of the scope within the body to be tracked (in theory). In this case, it may be desirable to provide the scope with a laser pointer or similar device to serve as a "target designator" to mark a point, determined by an MRI or CT scan, and so guide the surgeon in placement of the shaft-tip tools.

The scope can carry ultrasound to continuously monitor the distance to ultrasound transponders attached near the shaft tips, allowing continuous tracking of tip motion.

If the scope is fitted with magnetic induction sensors by means of which scope position and orientation (or, at least, scope tip position and orientation) can be determined to high accuracy with respect to an external coordinate frame. In some cases it may be desirable to register or calibrate with respect to positional information referenced to an external frame, such as data obtained via an MRI or CT scan. In this case, the scope might be used to relay such information to the surgeon, perhaps via use of a laser-pointer type device which can be aimed with reference to the external coordinate frame to designate a particular spot within the patient's body. The surgeon could then move the laparoscope scope and shaft-mounted tool with relation to the designated spot.

It is also possible that the scope could be fitted with some type of transponder, for example, an ultrasonic transponder, to continuously monitor the position of the shaft-mounted laparoscope tools and thus track their position and orientation with respect to an external reference frame.

Stereocamera—If an umbilical is not needed, an alternative use for the temporarily idle scope would be to insert fiberoptic imaging bundles, each equipped with a GRIN lens, through the scope working channels, to provide a stereo image of the surgical site. The imaging-bundle can be withdrawn to remove and replace a tip, then re-inserted for the next procedure.

Use of scope for stereoscopic imaging: After transfer of the tip tool to the laparoscope shaft, the two working channels of a standard NOTES scope are free. Coherent fiberoptic imaging bundles, to the distal end of each of which is attached a GRIN or similar lens, can be inserted into the working channels to deliver a stereoscopic image of the surgical site during the procedure. The FO bundles will then be removed following the end of each surgical step to allow tip exchange.

The scope may incorporate a camera to provide a video image of the surgical site. Because the techniques proposed here relieve the scope of much responsibility during the actual performance of each step in the surgery, more room is potentially-available at the distal end of the scope, permitting (for example) incorporation of a stereo video camera at the scope tip, to provide a stereo video image of the surgical site.

Haptic Feedback

There are complaints that, even in laparoscopic surgery, friction at the trocar or elsewhere limits the surgeon's haptic sense—the ability to palpitate and "feel" the tissue. Tools have been designed to incorporate a variety of "haptic" sensors, typically a Maltese-cross or hexapod arrangement of strain gages interfaced to a specialized joystick or similar means to provide "force-feedback" to the surgeon.

Haptic feedback: The current proposal for the first time permits use of large-diameter tools with minimal-incision size. Surgical tools have been designed to incorporate force-torque feedback, but such tools are currently much too large to use for laparoscopic surgery. The "modular minimally-invasive" technique proposed here will permit such tools to be used and thereby provide "haptic feedback" to the surgeon, enabling him to palpitate tissues, etc. Many methods have been devised to report and "display" the term includes "tactile display"—haptic information to the surgeon. This may involve specialized regions at the proximal end of the shaft, in contact with the surgeon's hands during the procedure, such as tactile display pads or other means.

Tool and/or fixture fabrication process: Conventional MEMs processing, such as (i) bulk silicon or (ii) surface micromachining is currently incapable of realizing mechanical elements capable of delivering forces >1 N and torques on the order of several 100 N-mm. It is most likely that micro-fabrication techniques such as (i) LIGA, (ii) EFAB (Microfabrica), or (iii) multi-layer micro-stereolithography (EoPlex) will be required.

Despite impressive progress in the fabrication of micro-mechanical parts midway between MEMs microdevices and conventionally (micro-) machined parts, tools with integrated haptic feedback and/or wrist mechanisms are likely to remain too large to pass a 5 mm incision. A primary benefit of this proposal is to make it possible to use such tool tips in conjunction with the familiar rigid laparoscope shaft.

It is anticipated that, to support the use of tools with integrated haptic-feedback sensors, or with wrist mechanisms providing additional degrees-of-freedom, some modifications to the proximal end of the shaft will be required, to provide haptic feedback to the surgeon's hands (controlling the shaft) or a wheel or thumb-operated element to control wrist orientation.

TrEndo (Lieden University) is one system designed to provide haptic feedback during laparoscopic procedures.

BenHani et al (Rennselaer Polytechnic) "Plug and play tool handles for laparoscopic surgery simulations" is another.

This University of British Columbia course by Sideny FeIs provides a good overview of haptic interfaces.

Consideration Re Tip-Shaft Coupling and Tip Mechanism Actuation

Mechanical Design Issues

Shaft Design

The shaft has to have sufficient rigidity to support the tip against reaction forces and torques generated by the surgical procedures. Since the flexural rigidity of a shaft increases with the fourth-power of the diameter, it is likely that the shaft will be a cylindrical tube surrounding and enclosing any additional mechanical elements, cables, etc, required to communicate with or actuate the tip mechanism If mechanical means are used to actuate the tip (no motors involved) then this might be accomplished by rods sliding within the shaft and pushing or pulling on elements in the tip, or it might involve rotation of rods within the shaft, engaging and rotating elements in the tip.

The present invention may optionally use of micro-motors, hydraulic or pneumatic mechanisms, and/or mechanical transmission from shaft to tip. For example, cable-driven mechanisms and/or four-bar mechanisms may be used.

When tool function involves relative motion of tool elements—such as the motion of one grasper or clamp jaw against another—this mechanical motion can be supplied in many different ways, for example, directly via (i) any combination of rotational and/or translational motion across the interface between shaft and tool, such as involving a shaft rod pushing on a tool element, or a shaft rack gear engaging a tool pinion gear (or vice versa), or a shaft miter gear engaging a tool bevel gear, or a shaft pinion gear engaging a tool internal gear (or vice versa).

One thing regarding the Faulhaber and other DC micro-motors (below) is that they incorporate micro-fabricated gearboxes. If the tip can contain such a gear mechanism, it may be unnecessary to also have a motor. The shaft may contain rods with micro-bevel gears or splines cut into the end which slide into and engage gears at the tip. Or a rod may have a rack gear cut into the distal portion of the rod, which engages a pinion gear at the tip. In this case, sliding the actuator rod relative to shaft and tip will rotate the pinion gear to actuate the tip mechanism. Or the rod can have a worm gear cut into the distal end, which engages a spur gear at the tip. In this case, the rod worm gear can be threaded into the tip gear after shaft-tip mating.

A second point is that motors usually consist of an element—the "rotor"—which rotates within a fixed "stator". Now the rotor and stator can be separated. If the stator carries the magnetic field coils, it might be attached to the shaft, while the rotor—which might contain permanent magnets, etc—is part of the tip. During assembly, the stator will slip over the rotor. No electrical connections are required to the tip in this case. Power transmission occurs via magnetic-field coupling from shaft-stator to tip-rotor.

Common shaft drive, multiple tip functions: A gear~for example, an internal or external gear machined into a rod contained within the shaft—can engage multiple gear mechanisms within the tip. If each tip gear is provided with a selectively-actuated clutch mechanism (for example, an electro-magnetic clutch) then it becomes possible to selectively activate one or another mechanical element of the tip and thus perform any of a number of mechanical functions using a common drive rod.

Or mechanical action can be generated using electromagnetic means, such as a DC motor, stepping-motor, or variable-reluctance motor. In this case, it is not necessary that the motor be entirely contained within the tip. Motors consist of a stationary element (the "stator") and a rotational element (the "rotor"). The rotor might be part of the tool and slip into a shaft-mounted stator element, containing the electrical drive coils, at the time tool and shaft are mated. In this, energy passes from shaft to tip via the magnetic fields created in the rotor-stator gap. The same principles apply to DC motors, stepping-motors with permanent-magnet as well as variable-reluctance rotors, and similar devices.

Shaft-to-tip power transmission: Motors of all types typically consist of a moving element for example, the rotor of a DC motor and a stationary element, such as the stator of a DC motor. In some cases these elements are in close proximity but not in mechanical contact. In such cases, power is transmitted from one element to the other via magnetic or electrostatic fields. In other cases, such as the "inch-worm" motor, the stationary element may contain clamps or other mechanisms which briefly attach to and exert mechanical force on the movable element. We note that the movable member of either of these types of motor may be contained within the tip, while the stationary member of the motor is contained within the shaft (or vice versa). For example, the stator and coil assembly of a microminiature motor can be part of the shaft while the rotor is part of the tip. These elements will be arranged so that, when tip and shaft are mated, the stator is concentric with the rotor and in the correct position for electromagnetic fields to act on the rotor to exert torque on elements of the tip. A similar type of arrangement would allow "inch-worm" type piezoelectric elements in the shaft to drive a rotating disk which is part of the tip.

It is also possible to transmit mechanical work via friction between two parts in contact. The piezoelectric "inch-worm" motor uses this principle. An inch-worm mechanism can be used to transmit force or torque from shaft to tool, if the tool contains a movable part engaged by an inch-worm like clamping mechanism attached to the shaft. The movable part can be a disk, to transmit rotational motion, or a shaft (as in the SQUIGGLE motor, New Scale Technologies, Inc.). Piezoelectric "wave" motors utilize the same principle and can be applied here in a corresponding manner.

"Inch-worm" type mechanisms containing textured or otherwise specialized contact elements can deliver greater force. These are sometimes referred to as "meso-scale" actuators.

For example, wire stubs attached to movable elements of the tip can protrude from the mating surface of the tip. Individual piezoelectric "inch-worm" clamp mechanisms can be provided within the shaft for each tip stub. When tip and shaft mate each tip stub will insert within it's corresponding clamp mechanism. Once mated, electrical connections within the shaft extending to each clamp mechanism allows the generation of an axial tension or push on the corresponding tip stub wire. The stub wires may simply attach to movable elements of the tip, or to a flexure mechanism to amplify stub wire displacement or force. The tip mechanism is simple and inexpensive while most of the complexity and cost reside within the shaft.

Inductive coupling: To eliminate the need for electrical contacts between shaft and tip, induction coils on the shaft and tip can be used to transmit electrical power from shaft to tip as well as to transmit and receive control signals.

Shaft-to-tip power transmission, rotational, key or spline: The shaft carries one or more control rods. Micro-machined into the end of each rod is a key or spline which can engage with a mating surface within a rotational element of the tip. These rods pass through bushings in the shaft which align each rod with the appropriate rotational element of the tip when tip and shaft are mated. Rotation of a control rod will then actuate a particular element of the tip.

Shaft-to-tip power transmission, rotational, bevel or miter gear. As above, except that the each rod carries a miter gear at the distal end, which mates with a 90 deg bevel gear, to transmit shaft rotation to elements within the tip.

Shaft-to-tip power transmission, rotational, worm gear. As above, except that each rod carries a worm gear at the distal end, which threads into a mates with a helical gear within the tip. Rotation of the rod will again transfer torque to an element of the tip.

Shaft-to-tip power transmission, translational, rack. As before, except that in this case, the distal end of each rod carries a rack gear which engages a pinion gear in the tip when tip and shaft are aligned and the rod is extended. In this case, translational motion of the rod will cause rotation of the tip pinion to actuate a tool or catch.

Shaft-to-tip power transmission, wobble-plate. In this case, three rods are provided within the shaft which pass through bearings spaced at 120 deg intervals and equidistant from the axis of a "wobble-plate" or eccentrically mounted disk within the tip. Extending and/or retracting the rods in the proper sequence will then cause clockwise or counter-clockwise motion of the wobble plate.

Wobble-plate, hydraulic actuation: As above, except that, instead of rods extending the length of the shaft, three hydraulic cylinders at the distal end of the shaft apply force to rotate the wobble-plate.

Another type of mechanism to transmit mechanical motion from shaft to tip is the "wobble-plate" motor. An offset disk, rotating (or driving) a shaft in the tool, is acted upon by three shaft push-rods passing through bushings spaced at 120 degree intervals with respect to the rotational axis. Extending or retracting the shafts in the appropriate sequence will cause the disk to rotate clockwise or counterclockwise, as desired. This mechanism is commonly-used in piston-type hydraulic motors. The mechanism is simple and requires no attachment—the push rods would simply slide into guide bushings in the tip at the time of mating.

Finally, a very interesting class of motors are those which involve friction drive. The inch-worm is a well-known example. These operate using two (typically piezoelectric) clamps which are actuated in alternation. Now in this case the movable portion—which can be a rod or a disk—can be attached to the tip, while the expensive clamp mechanism can be attached to the shaft. Piezomotors used for camera focusing are a variant on this design, using a "wave" or harmonic-drive mechanism. More information is provided below.

It may also be useful to note that there are now a number of references to "mesoscale actuator devices" (MAD), which appear to be inch-worm mechanisms, adapted to provide high forces and torques via micro-machined grooves or serrations: 100 pound drive forces have been achieved!

"Mesoscale actuator devices": Inch-worm or friction drives typically involve mating elements which are smooth. Surface textures can be applied to the mating surfaces to increase actuation forces or torques obtainable. Such devices are sometimes designated "mesoscale actuators".

Docking Station

To retain the tool upon delivery to the distal end of a scope or a NOTES delivery tube, a "docking station" may be incorporated into the design or attached to the distal end of the scope or tube. The functions of this docking station will be to (i) "catch" the tool as it is delivered through a scope working channel, (ii) to support any pulley or cable mechanism, involving joint use of two scope working channels, (iii) to hold the tool in place during alignment and mating, (iv) to (controllably) release the tool, or capture it when it is released back to the scope after use. The docking station may also incorporate functions to rotationally-index the tool and so orient it correctly for pick-up by the shaft. Also to hold the docking station may include a mechanism for holding it in a stable position within the surgical site. For example, a mechanism can affix the cassette within the abdominal cavity so that it provides a stable tray for the tools and does not flip over when it lays over the small intestine or other organs. There could be a mechanism that can open and close and function as support legs or like a wire base. The docking station could also be attached along the side, for example on internal abdominal wall, etc.

Docking module: A specialized region or attachment to the scope or tube may be provided which will serve one or more of the following functions: (i) "catch" the tip when it is delivered through the scope working channel, (ii) rotationally index the tip, (iii) provide an elastic or releasable detent to affix the tip to the docking module, (iv) to retain the tip and resist forces generated during the process of aligning and mating to the shaft, (v) (controllably or passively) release the tip to the shaft, as well as any or all of these operations, performed in reverse. If controllable latches or release mechanisms are required, any of a variety of means may be provided, such as an electrical solenoid latching element, a hydraulic or pneumatic latch or clamp, etc.

While this may not be necessary, it seems likely that some type of specialized fixture, located at the distal end of the scope or tube, is likely to be required (or at least helpful) to: (i) catch the tip when it arrives at the end of a working channel or overtube during the "tip delivery" phase, (ii) retain the tip while the laparoscope and/or scope are manipulated to orient and align tip and shaft prior to mating, (iii) to hold the tip somewhat firmly in place during contact and mating of shaft and tip, (iv) to hold the tip when it is returned from the shaft to the scope and to (v) retain the tip while during and after its release from the shaft.

Since scopes are expected to be available from a number of manufacturers, it may or may not be desirable to either (i) license the docking station design to scope vendors or (ii) provide a small module which can be mounted to any of a number of existing scopes, adapting them to use this new technology.

The docking station may or may not also provide means, such as an electrical connector, to mate with the similar means, attached to the shaft, to supply energy or transmit control signals between shaft and tip. In case the docking station is to be installed at the tip of the overtube, this might be arranged via an expanding ring mechanism, possibly actuated pneumatically, which will expand against the interior surface of the overtube, thus locking the docking station in place. The docking station might have transparent regions to allow use of a scope camera and illumination system during surgical placement of the scope.

Mating connector—For example, the tool may present a pin to engage and be retained by a collet-clamp affixed to the end of the laparoscope shaft. The collet may provide a clamp-and-release mechanism, or (alternatively) an undersized elastic collet can retain the pin via elastic clamping forces after it is pushed into engagement.

If a threaded coupling is used to attach tip to shaft, then it may be important to choose either a left- or right-hand thread, so that reaction torques don't cause the tip to unscrew from the shaft.

A very wide variety of other mechanisms can be used to attach tip to shaft. For example, a pin might protrude from the mating end of the tip while the shaft end will carry a chuck or collet. During the mating operation, the shaft is manipulated to (i) align or make parallel the axes of pin and collet, (ii) offset tip and/or shaft into the axes are coincident, (iii) advance the collet to engage the pin. An elastic collet, slightly smaller in diameter than the pin, will expand slightly to retain the pin (and tip) after the tip is withdrawn from the docking-station. Or it may be desirable to equip the collet with a latch-and-release mechanism, controlled by the surgeon.

If the pin is hollow, the pin lumen might be used to transfer pneumatic pressure from shaft to tip to energize or actuate graspers or scissors. For example, the tip could utilize a micro-miniature electroformed bellows, attached to and terminating the pin channel.

Application of pressure to a port at the proximal end of the shaft will then cause the bellows to expand and extend, thus applying force to mechanical elements within the tip tool and thereby actuating graspers or scissors. Spring return, or suction applied to the proximal end of the shaft, would then cause the bellows to contract and return the tool to its initial state.

Mating connector (pin-and-socket): A pin may protrude from the mating surface of the tip. The shaft will carry a collet mechanism of approximately the same inside diameter as the outside diameter of the tip pin. During tip transfer the surgeon will orient and align the collet axis with the pin axis, advance the shaft to move the collet over the pin, and then engage the collet clamping mechanism, thereby retaining the pin and allowing the tip to be removed from the scope working channel. The process will be reversed when the tip is returned to the scope working channel for exchange.

The internal diameter of the collet can be slightly undersize and the collet mechanism compliant, so that application of a slight axial force when collet and pin are aligned is sufficient to push the collet over the pin and afterwards retain the pin due to the elastic clamping force exerted by the collet. In this case, no open- and release mechanism is required of the collet.

To permit a sufficient amount of slack during the alignment task, pin or collet may provide a short tapered region, to act as a guide to bring tip and shaft into more accurate alignment than is otherwise possible.

The pin may be hollow, allowing actuation means, such as push rods to pass through the pin from shaft to tip, thus allowing the translation or rotation of control rods within the shaft to exert forces and/or torques on mechanical elements within the tip—including splined hubs, pinion gears, bevel gears, etc and thus actuate tip tools.

The pin may be hollow and attached to an elastomeric or, preferable, an electroformed metal bellows within the tip. The shaft collet will be connected to a hydraulic line. When tip and shaft are mated, pressurizing this control line will cause the bellows to expand and exert force on elements within the tip.

For example, the tool may present a pin to engage and be retained by a collet-clamp affixed to the end of the laparoscope shaft. The collet may provide a clamp-and-release mechanism, or (alternatively) an undersized elastic collet can retain the pin via elastic clamping forces after it is pushed into engagement.

Alternatively, the tip may be the female part, while the shaft male connector expands during the mating process to retain the tip after release from the docking station.

If it is not possible to align tip and shaft appropriately prior to mating, a connector, such as a spherical ball on a stud, captured by a mating "clamp" on the shaft (or vice versa) may be required. This type of connector could be engaged by a shaft approaching from any direction. Whatever type of connector is used, it is likely to be desirable to provide a tapered "lead-in" region which will tolerate some degree of initial misalignment and then "guide" the tip and shaft mating parts into proper alignment for mating.

Ball-and-stud coupling. In some situations it may be difficult to align the tip and tool axes parallel. In this case, in place of a simple pin, the tip mating surface can be provided with a ball-and-stud. In place of a collet, the shaft will carry a clamp designed to mate to and retain the ball. In this case, the shaft may approach the tip from a wider range of directions. This will also allow the tip to be mounted at an arbitrary angle, without the need for a laparoscopic "wrist" mechanism, if it is desirable to have the tip offset for the surgical procedure.

Magnetic latching mechanisms: If the shaft is fabricated from a material with high magnetic permeability and a movable element within the tip is also of high permeability, bringing a permanent magnet near or into contact with the proximal end of the shaft will cause a force to be exerted on the tip element, acting to bring the tip element into closer proximity or contact with the shaft element. This method can be used to actuate a tip mechanism or to engage or disengage a mechanical latching element within the tip.

Electro-magnetic latching mechanism: As above, except that a coil is wound around the proximal end of the shaft. Passing a current through this coil will induce a magnetic field within the shaft, which will act in the same was as described above to actuate the tip element. Micro-miniature electromagnetics may be utilized for connection and/or actuation of the tip.

Magnetic fluids: A magnetically-actuated clutch can be realized using a dispersion of magnetic colloidal particles filling a gap between two closely-apposed surfaces. A clutch mechanism of this type, incorporated within the tip tool, can be activated using the same techniques indicated above.

If the tip and/or shaft are either (i) manufactured from a material with high magnetic permeability or (ii) either contains a miniature magnet (such as a SmCo or NdFeB magnet), magnetic forces may be used to assist with the retention of the tip to shaft. In this case, it is possible to provide a "release" mechanism via a small coil placed at the end of and around the shaft. A current-pulse through this coil will transiently generate a reverse magnetic field, allowing tip and shaft to be disengaged. If shaft and tip are made of a material with high magnetic permeability, another means to releasable engage and disengage the tip is to simply move a magnetic into contact with the proximal end of the shaft, using (for example) a simple mechanical switch or button, controlled by the surgeon with his thumb. When the magnet is in contact with the proximal end of the shaft the magnetic field is carried by the high-permeability shaft to the tip, drawing the tip into contact with the shaft. In this case it is important that shaft and tip material have low magnetic retention, so that the magnetic field vanishes once the magnet is moved away from the shaft.

If the shaft is provided with helical external "threads" to facilitate insertion of the shaft through the incision in the skin, it is possible that this same threaded region could insert into a complementary surface of the tip end to attach tip to shaft.

Another means of capturing and mating tip to shaft may involve passing a wire to which a Tee-shaped ferrule is attached at the distal end, along the axis of a (hollow cylindrical) shaft, inserting it through a slot in the tip, rotating the wire 90 degrees to engage the tip, and then applying tension to the wire to retain the tip to the end of the shaft. The tip can then be released after return to the docking-station by reversing the procedure. While in general it is likely that the mating surfaces will have conjugate profiles (such as pin-and-hole) there are cases where the mating surfaces may have identical form (so-called "hermaphrodite" connectors). It is likely that any collet mechanism required can be machined into a "one-piece" shaft via EDM or similar means, to create a notched "flexure" mechanism.

Flexures and compliant mechanisms: In many cases it is possible to realize rotational and translational elements by means of one-piece machining of notches to create a so-called "flexure mechanism", also known as a "compliant mechanism".

Flexures mechanism, push-rod actuated scissors or graspers: Flexure mechanisms can be designed with integrated "levers" to provide substantial amplification of displacement. A flexure-type scissors or grasper can be fabricated from one piece integral with the tip and actuated by a single push-rod extended from tip to shaft to bear on a movable element of the flexure.

Tip fabrication—Micro-fabricated tools containing a multiple-degree-of-freedom "wrist" mechanism are available, but these tools are also much too large to pass through a laparoscopic incision. Because they are, however, small enough to be delivered through a scope working channel or overtube, tools with integrated wrist mechanisms will also be usable with the technique proposed here.

Micro-fabricated tools containing force-torque sensors, capable of providing haptic feedback to the surgeon, are also possible, but too large to pass through a laparoscopic incision. Again, this type of tool will be usable in the new approach proposed here, making it possible for the first time to supplement the haptic feedback naturally provided by the rigid shaft. In many cases the haptic sense which, in theory, is provided by use of rigid laparoscopic tools is limited, due to friction and other effects arising due to interaction between the shaft and trocar.

There are a wide variety of possible mechanisms or elements by which the tool can reversibly mate with the shaft while also providing sufficient rigidity to remain stable against the reaction forces and torques associated with use of the tool. These mating elements support one or more of the following functions: (i) "guiding" the mating pieces into good contact (thus relaxing the precision with which the parts must be oriented and aligned prior to mating), (ii) a "detent" or catch mechanism, which may be activated by an independent mechanism to engage or release, or (alternatively) the catch or detent function may be achieved passively, through the use of an elastic mechanism, (iii) means by which mutual motion or rotation of the mating parts is restricted. For example, insertion of a pin into a matching hole removes four of the six relative degrees-of-freedom of the two parts, leaving only free rotation about the axis of the pin and translation parallel to that axis. Many such kinematic or "semi-kinematic" constraints can be incorporated into shaft and tool to fix their relative position during the surgical procedure. In some cases, the parts are not completely constrained by kinematics: instead, frictional forces or clamps may be used.

In other cases, suction may be used to retain tool to shaft.

In other cases, a specially-shaped wire rod (for instance, with a Tee-bar end) can insert into a tool slot or other specialization to engage the tool, so that tension on the wire holds the tool in place against the shaft.

A "detent" mechanism, such as a latch engaging a machined slot in the pin, can be used to restrict axial motion of a pin-and-collet mechanism. Such a detent will also provide a mechanism to retain the parts in contact, after insertion of the pin into the collet, as well as to allow for the controlled disengagement of pin-and-collet.

A cam or wedge action can be used to separate the parts axially and assist disengagement.

If it is necessary to attach the tool in a precise position and orientation with respect to the shaft, a kinematic coupling, such as a Kelvin coupling, can be used. In this case, a magnetic field may be used to retain contact between tip and shaft during the surgical procedure. This may involve use of a tool and shaft fabricated from a material with high magnetic permeability. In that case, a magnetic field induced in the shaft by means of a permanent magnet brought into contact with the proximal end (surgeon's end) of the shaft, or by means of a coil wound around the proximal end of the shaft, will cause the tool to be attracted to shaft. The tool will release when the magnetic field is removed.

Conventional MEMs fabrication processes are discussed in many texts 5 and are often classified as "surface" or "bulk" methods. The force and torque available to date from devices fabricated using either of these processes are much too limited to actuate microsurgical tools, which require forces on the order of 1 N and torques of 100-300 N-mm. "High aspect ratio" processes such as LIGA and EFAB have been developed to create micro-mechanisms of the appropriate scale, mid-way between conventional MEMs devices and surgical tools fabricated by standard machining and molding methods.

Hydraulic mechanisms can provide large forces while also offering high precision. Micro-fabricated bellows, such as electroformed bellows mechanisms used in micromanipulators, can be used to actuate elements within the tool. Hydraulic or pneumatic pressure can be applied to such a mechanism via a hydraulic coupling. For example, if a pin-and-collet mechanism is used to mate tool and shaft, the pin can be hollow, and attach to a bellows mechanism within the tool. It is then possible to apply hydraulic pressure to actuate the bellows via a conduit attaching to the collet and running the length of the shaft. If hydraulic or pneumatic connection to the tool is provided, multiple hydraulic mechanisms can be supported with use of micro-miniature hydraulic valves (which can be actuated electrically, or via magnetic influence from the shaft).

Tip tool actuation, hydraulic: Use of an umbilical cable will allow hydraulic actuators within the tip to be energized, without requiring hydraulic-disconnect couplings between shaft and tip. Use of hydraulic actuators permits the generation of large forces while at the same time allowing very precise movement, as is well known from experience with hydraulic micropositioners used for micro-electronics workstations as well as for electrode positioning in neurobiology.

Tip tool actuation, hydraulic: Micro-fabricated hydraulic valves are becoming available which might be integrated into the tip. In some cases these valves may be magnetically actuated, allowing use of techniques indicated below to communicate the magnetic activation force from shaft to tip. Use of multiple micro-hydraulic valves within the tip allows a single hydraulic or pneumatic supply line or plenum to selectively activate hydraulic or pneumatic effectors within the tip.

Micro-Miniature Piezoelectric Motors

Most piezoelectric devices manufactured today use polycrystalline materials such as barium titanate. Also under development are single-crystal piezoelectric materials which have greatly improved operating characteristics.

Seiko is also a major vendor of ultrasonic motors for camera and cell-phone applications. They market this 4.5 mm×2.5 mm ultrasonic motor. NewScale is manufacturing the SQUIGGLE ultrasonic linear motor, which can move a 7 mm/sec and generate 30 gm [0.3 N] force. The motor dimensions are 1.8×1.8×6 mm. The motor is used in a Tamron zoom lens.

Air Lock

To maintain pressure in the peritoneal cavity during tool-exchange, it may be desirable to provide some type of air-lock at the proximal end of the scope. To facilitate rapid exchange of tips, an air lock may be provided or fitted to the proximal end of the scope, to prevent the release of pressure within the peritoneal cavity from occurring during tool exchange.

Inch-Worm Tip Delivery

In addition to draw cables and pneumatic delivery mechanisms, it would also be possible to have an "inch-work" pusher or "tractor" carry or push the tip to the end of the scope, and retrieve the tip after use. It would also be possible to use something like the "rolling-stent" drive mechanism:

Disposable tips: Separation of function between tip and shaft may lead to significant cost reduction for the tip mechanism. In this case, the tips become a "disposable" element, discarded after the procedure, and thus eliminating the need for additional sterilization.

The modular nature of the tools made possible by this proposal allows a much greater variety of tool types than are currently utilized in laparoscopy. It is possible, for example, to envision tools utilizing integrated diode lasers, for photodynamic therapy, or optical cauterization; RF cautery; tools incorporating devices for sensitive electrophysiological measurements including, for example, mapping of cardiac magnetic fields; devices for delivery of aerosols, including an ice-mist to cool tissue, or to deliver drugs.

We anticipate that the separation of function between shaft and tool made possible by the present invention will lead to significant reduction in the complexity and manufacturing cost of the tools, in many cases reducing tool cost to such an extent that the tool is disposable after use for a single surgical procedure. The cost and risks of re-sterilization of tools may thereby be eliminated.

In some cases it may be convenient to optically-couple control signals from shaft to tool, utilizing one or more selectively-activated photosensitive elements located within the tool, to switch various electrical functions on and off within the tip.

In other cases, it may be possible to use selectively activate various functions within the tool through use of an RF-ID tag located within the tool and excited by a transceiver in proximity to the patient.

In other cases, it may be possible to selectively-actuate mechanical elements within the tool comprised of shape-memory or similar alloys exhibiting a mechanical phase change, via an optical signal coupled via optical fibers contained in the shaft but terminating in proximity to the elements to be activated.

FIGS. 40-60 illustrate specific implementations of endoscopic instrumentation for both handheld and robotically assisted tools, where the tool tips 64, such as graspers 30, scissors 35 and retractors 38, including needle holders and other actuated as well as not actuated end effectors, are interchangeable within the surgical cavity and to a common handle 73 that is either handheld or robotically enabled 21. Furthermore, these tips are accessed and may be stored while not engaged to the handle, within the surgical cavity. The action of engaging the end effectors 1, 64 happens within the cavity enabling the handle tube 55 or part of the handle tube to remain within the surgical space throughout the duration of the exchange. The tip size and type is expanded because the tips 64 may be inserted through a different and larger port than the handle tube 55.

Securing the Base Tube

Figure 40:
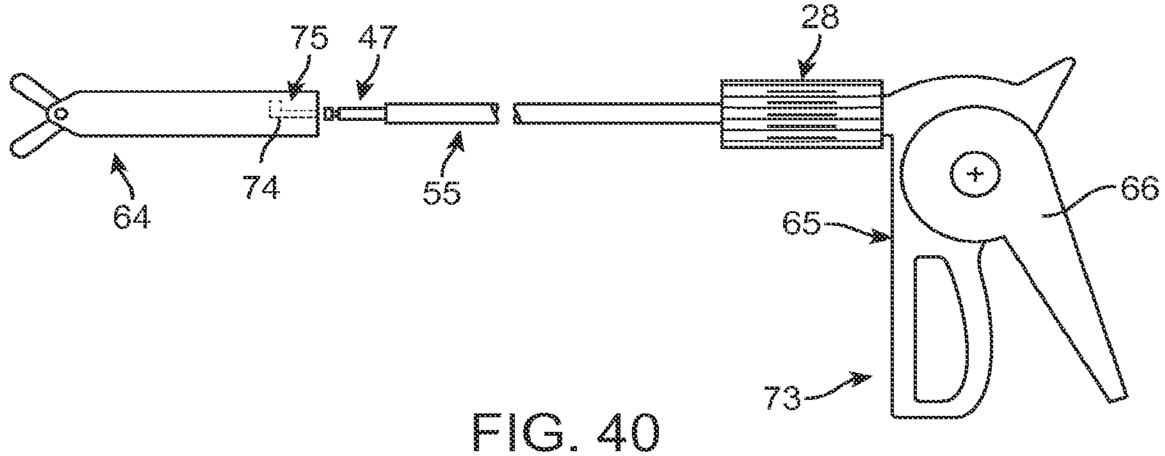
FIGS. 40-42 illustrate a manually operated surgical tool according to the present invention.
Figure 41:
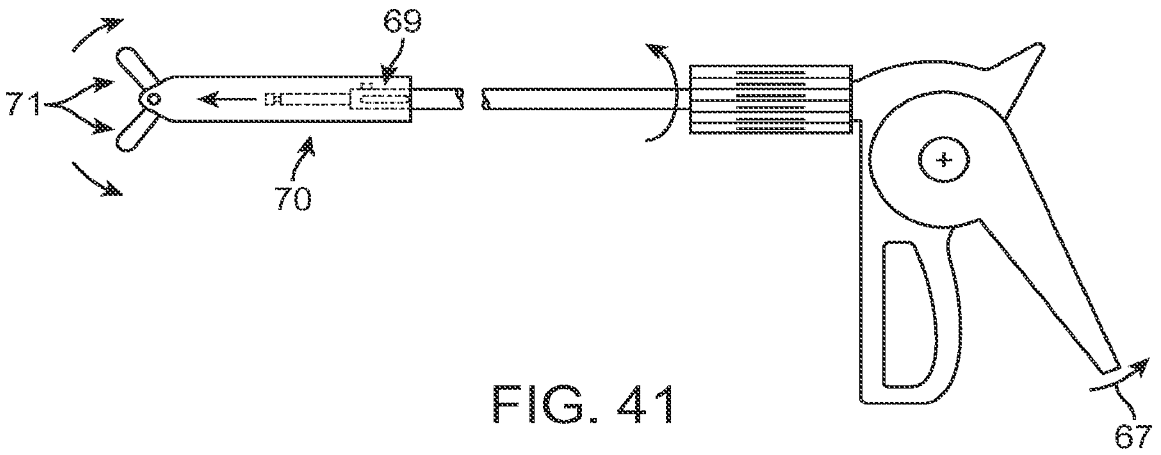
Figure 42:
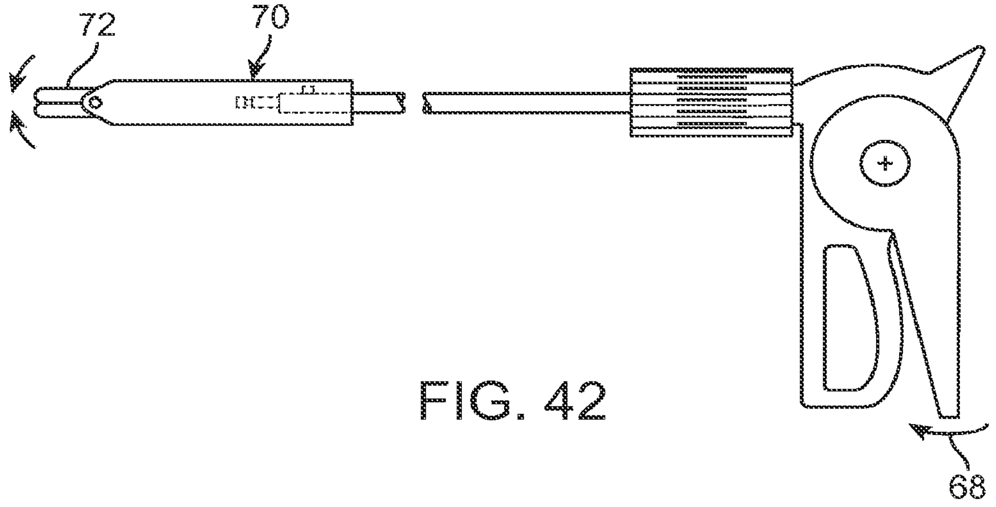

The basic concept has a handle 73 that engages to a tip 64 through a mechanism that secures the actuated and non-actuated components between the handle 73 and tip 64. The tube 55 aligns a "T" engagement boss 54 that slides into the tip slot 74 which has a preferred position slot 75, as shown in FIG. 40. When the "T" engagement boss 54 meets the preferred position slot 75, as shown in FIG. 41, the tube rotation handle 28 is rotated such that the tube 55 and "T" engagement boss 54 rotate into a locked position within the preferred position slot 75. The handle 73 with the tip 64 attached is shown in FIG. 42. The opposite action is taken to disengage the tube 55.

Mechanical Tip

Figure 43:
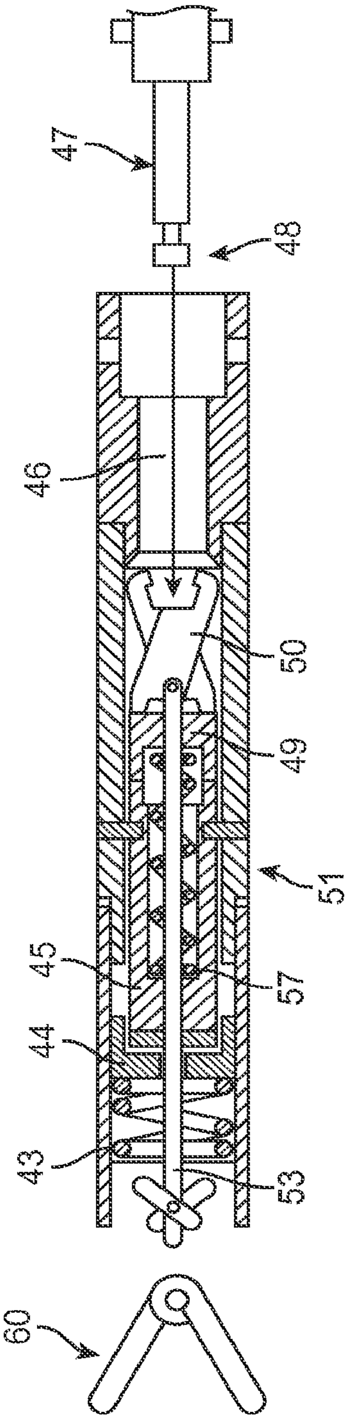
FIGS. 43-44 show a mechanical tip for the surgical tool.
Figure 44:
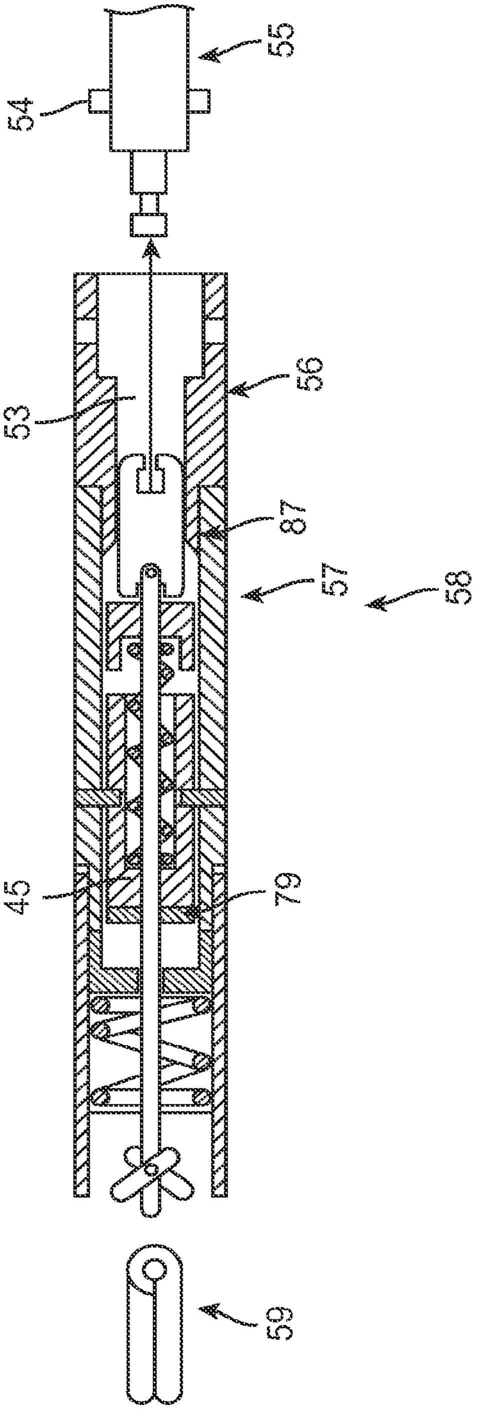
Figure 48:
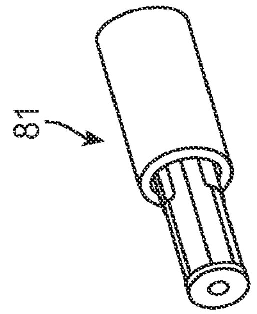
FIGS. 45-52 illustrate a mechanism for engaging and disengaging the mechanical tip.
Figure 52:
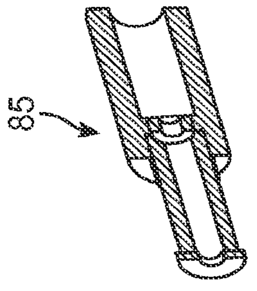
Figure 47:
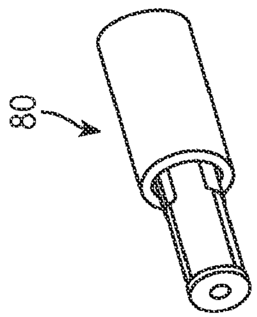
Figure 51:
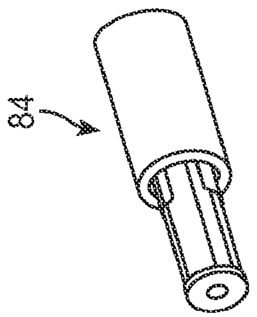
Figure 46:
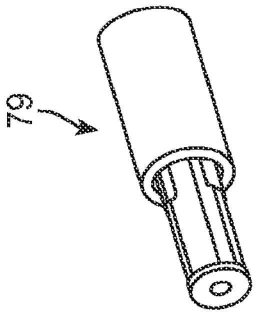
Figure 50:
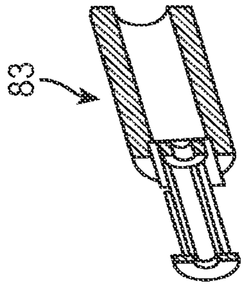
Figure 45:
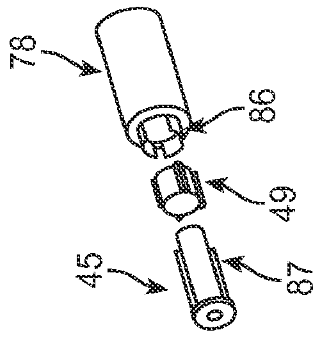
Figure 49:
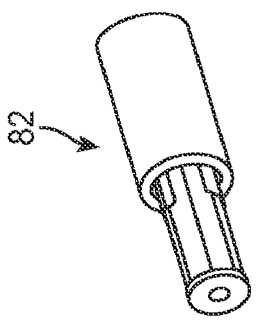

FIG. 43 shows a mechanical tip 64, and with the tube 55 in a locked position 69, the handle shaft 47 is extended by opening the handle lever 66 to a point that the jaws are beyond open 71. This action causes the handle shaft 47 to engage the shaft latch mechanism 58, as shown in FIG. 44.

The shaft latch mechanism has a similar action to the latching of some common retractable ball point pen where at one end there is a push button and the other, the writing side of the pen. By pushing the button, a latching mechanism toggles between a state were the pen position is set for writing or withdrawn. The action for engaging the mechanical tips 64 functions similarly where the handle shaft 47 is disengaged from the tip 64 in the first latch position; this latch position is similar to when the pen is extended and set for writing. The handle shaft 47 engages by extending the shaft 70 into the tip causing the latch 76 state to toggle; this is similar to the pen being retracted. Using this pen analogy, the actuation of the handle shaft 47 displacement for moving the jaws 2 would occur in the travel distance between where the pen is open and withdrawn. It is important to note that there are additional states and mechanisms interacting to enable the functionality of the invention that is beyond the simple analogy of the retractable ball point pen. This example is only given to bring the mechanism type into the light of common daily experience.

The following is a more detailed description of the process for engaging, operating, and disengaging the mechanical tip 42, illustrated in FIGS. 45-52. After the tube 55 is in a locked position 69, the handle shaft 47 is extended by opening the handle lever 66 beyond open 71. This action causes the handle shaft 47 to engage the shaft coupling 57 while in its open position 50 and move towards the shaft coupling 57 distally. The shaft coupling has a pivot that is connected to the tip shaft 63. The tip shaft 63 is coupled with the jaws 2 on its most distal end. The engage spring 43 acts over a short distance while the handle shaft 47 is engaging. The engage spring 43 provides the loading force needed to actuate the toggle action of the slide ratchet 45. The slide washer 44 holds the engage spring 43 at a specific preload and displacement so that the tip shaft 53 can freely move axial beyond the engagement displacement set by the slide washer 44. The slide ratchet 45 engages with the spin washer 49 and the toggle spring 52. When the shaft coupling 57 in its open state 50 moves distally by the action of the handle shaft tip 48, it pushes the spin washer 50 to engage with the slide ratchet 45. The spin washer 49, in contact with the slide ratchet 45, displaces the slide ratchet 45 distally, by pushing on the slide washer 44 and compressing the engage spring 43. The surface contact between the spin washer 49 and slide ratchet 45 are sloped such that an axial load between them will cause a rotation torque between the two parts. Both the spin washer 49 and the slide ratchet 45 are restrained from rotating by axial grooves and slots along the length of the ratchet housing 78. While in process of engaging to release 79 the slide ratchet fingers 87 slides beyond ratchet housing slots 86 allowing the slide ratchet to rotate to a released 84 position. With the return of the handle lever to the normal open position 66, the spin washer 49 moves proximal and the slide ratchet 45 finds the slot 86 and after the tip shaft 53 moves a small distance proximally, the snap ring 79 captures the slide ratchet 45 such that the slide ratchet 45 and the spin washer 49 move together as one unit.

Within the same handle lever to normal open position 66 action, the shaft coupling 57 moves proximally, and opposing teeth 86 on the proximal end of the shaft couplings 57 are forced to close around the handle shaft tip 48 by a shrinking of the inner diameter and the tooth obstruction 87 surface. The tip is now fully engaged with the handle 73. The range of motion is only limited by the length of the grooves and slots unoccupied and movement occurs without a spring load because both the engage spring 43 and toggle spring 52 are internally captured. The action of closing the handle lever 68 transmits a mechanical linkage to close the jaws, and vice versa. The tip 64 is secured to the handle and will not release until an opposite procedure of actions takes place.

Releasing the tip 64 requires a similar procedure as above. The tip 64 is placed within its holster not shown. The handle lever 66 is opened 67 so that the jaws go beyond normal open position 71. This action causes the shaft coupling 57 to slide into a larger inner diameter section of the housing and for the teeth 86 to disengage. The handle shaft tip 48 pushes through the shaft coupling 57 to the spin washer 49, and slides the slide ratchet fingers 87 beyond ratchet housing slots 86 and causing the slide ratchet to rotate from the engaged to lock 79 position to the ratchet to lock 80 position. The release of the handle lever 66 allows the engage spring 43 to move the slide washer proximally into a locked 81 position. The toggle spring 52 pushes on the distal ends of the shaft coupling 57 forcing the teeth 86 to expand allowing the handle shaft tip 48 to be released. The tube 55 is rotated to release the "T" engagement boss 55 from the proffered position slot 75. The handle 73 tube 55 and shaft 47 may now be removed from tip 64.

Robotic System & Electro-Mechanical Tips & Handles

Figure 53:
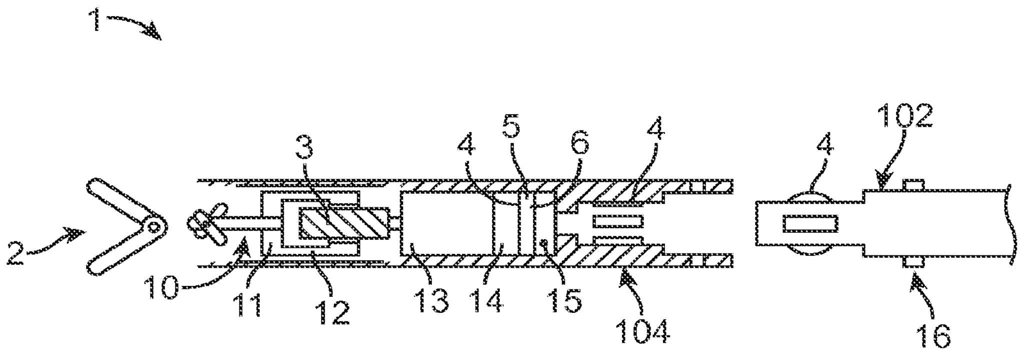
FIGS. 53-55 show a robotic system that includes electromechanical tips and electro mechanical handles.
Figure 54:
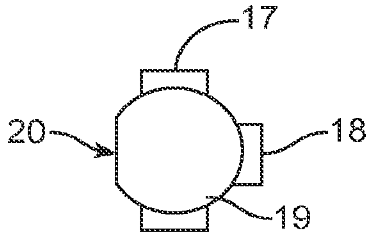
Figure 55:
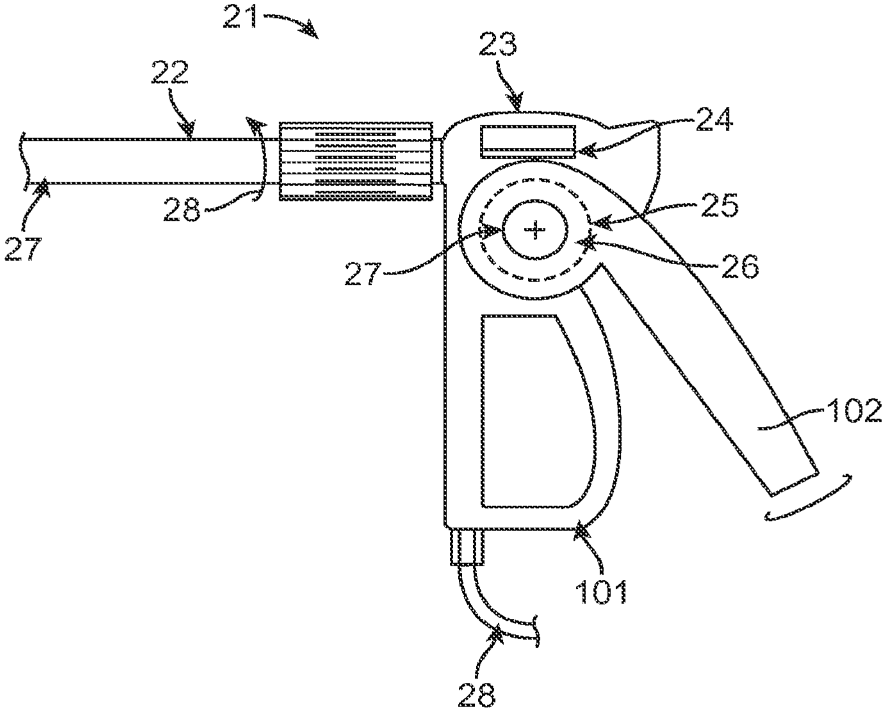

FIGS. 53-55 show a robotic system 100 that includes electro-mechanical tips 1 and electro mechanical handles 21 where the handles act as the master over the tips and the tips follow such that a master-slave relationship exists between the two axes of the system. The control and actuation are driven with real-time computation using a computer system with firmware and software to support the controls of a real-time master-slave system.

The electro mechanical tip 1 actuates a variety of tips through the axial displacement and actuation of a tip shaft 48. The tip shaft 48 is driven by a motor 13 with a lead screw 3 as a shaft coupled to a lead screw nut 11 connected to tip shaft 48 for actuating the jaws 2. The lead nut 11 slides on a bearing 12 surface that prevents rotation and allows axial motion. The motor 13 is driven by a printed circuit board 4 that has a controller chip with computer logic 6 and drivers 5 for controlling the action of the motor 13 and subsequently the jaws 2. The motor 13 uses sensors 14 for monitoring the position, velocity and load at the jaws 2. A battery 15 may be used for powering actuation and/or control of the motor 13. Radio frequency may be used within the printed circuit board 4 to communicate state in conjunction with the battery enabling cordless instrumentation. Sensors 14 may include but are not limited to: position sensors, POT/encoders, Ir/image sensors, velocity sensors, tachometers, force sensors, current sensors, and load cells.

Alternatively, a cabled power 17, ground 18 and a signal 19 for communication may be implemented through a connector 9 system. A flat for orientation 20 is included for proper alignment of male and female sides. The connector system may connect an electro mechanical handle 21 directly to the electro mechanical tips 1, or indirectly via a robotic system such as the DA VINCI system by Intuitive Surgical, Inc. In such a system a robotic slave arm would connect to the electro mechanical tip and a robotic master arm would connect to the electro mechanical handles.

A "T" engagement boss 16 is inserted in a slot 74 until it reaches a preferred position slot 75. The "T" engagement boss 16 is rotated until it finds its engaged position 69. The tube 103 rotates independent of the connector 9 system.

As shown in FIG. 55, the electro mechanical handle 21, has a handle 101 and a handle lever 102, with a motor 25 and gear reduction 26 system between them, such that the motor 25 can actuate the handle lever 102 relative to the handle 101. The motor 25 is driven by a controller printed circuit board/driver/logic 24 and uses feedback from sensors 27 measuring all or a portion of position, velocity and load, for the control and actuation of the handle lever 102. The electro mechanical handle 21 may be powered by a battery 23 and communicate through a wireless radio frequency, or be powered by a cable 28. Sensors 27 may include but are not limited to: position sensors, POT/encoders, Ir/image sensors, velocity sensors, tachometers, force sensors, current sensors, and load cells.

For the system where the electro mechanical handle 21 attaches directly to the electro mechanical tips 1, the tube 22 and the tube 103 are the same tube. The tube rotation handle 28 rotates the tube for connecting the "T" bar engagement 16 to the tip housing 104.

For the robotic system 100, the tube 103 connects to the robotic slave arm and the Tube 22 connects to the robotic master arm. For the robotic system 100 the cable 28 can be fed through the outer tube 22 and into the robotic slave arm.

End Effectors

Multiple jaw 2 types can be used in this invention. Conceivably, all single actuated mechanisms may be utilized. Fundamentally, the invention enables a coupling between tips that actuate with a base rod and pushrod. Tips that actuate using a base rod and a push rod may be controlled under this invention. Furthermore, end effectors that utilize electricity such as for cauterizing or where no secondary actuation is needed, may also be controlled. Several commonly used jaw types are described below as an example of some of the end effectors enabled by the invention.

Figure 56:
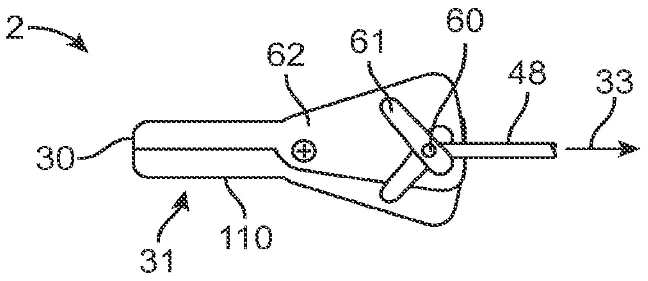
FIGS. 56-57 show a grasper or needle holder end effecter.
Figure 57:
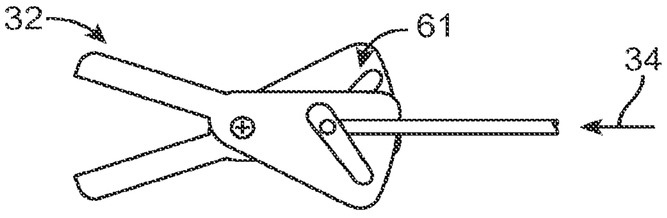

As shown in FIGS. 56-57, a grasper and/or needle holder 30 end effecter is actuated by the rod moving proximally or rod tension 33 and holds a needle or tissue with the grasper closed 31 while under tension. When the tip shaft 48 is moved distal or under compression the grasper is open 32. The pin 60 is connected to the tip shaft 48 and slides within the leverage slot 61 causing the grasper blades 110 to pivot around the pivot 62 and open or close.

Figure 58:
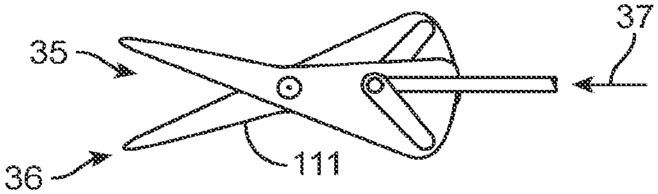
FIG. 58 shows a scissor end effecter.

As shown in FIG. 58, a scissor 35 end effecter works similarly to the grasper except the grasper blades 110 are replaced by scissor blades 111.

Figure 59:
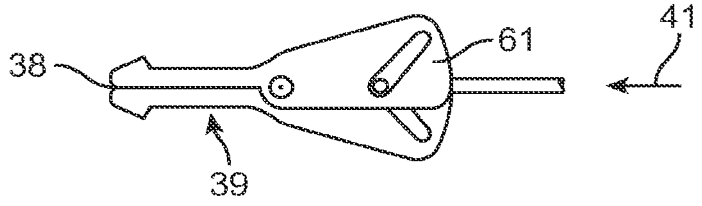
FIGS. 59-60 show a retractor end effecter.
Figure 60:
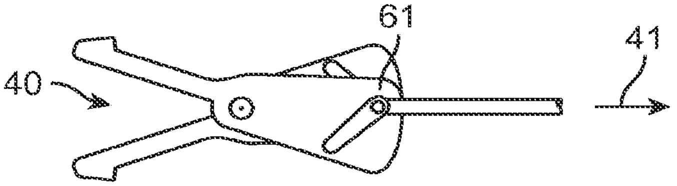

As shown in FIGS. 59-60, a retractor 38 end effecter works similarly to the grasper 30 as well, except the leverage slots 61 are angled in the opposite direction so that the movement and tensioning 41 of the tip shaft 48 causes the blades to open in tension 40 with a proximal motion and close 39 in compression with a distal motion.

Figure 61:
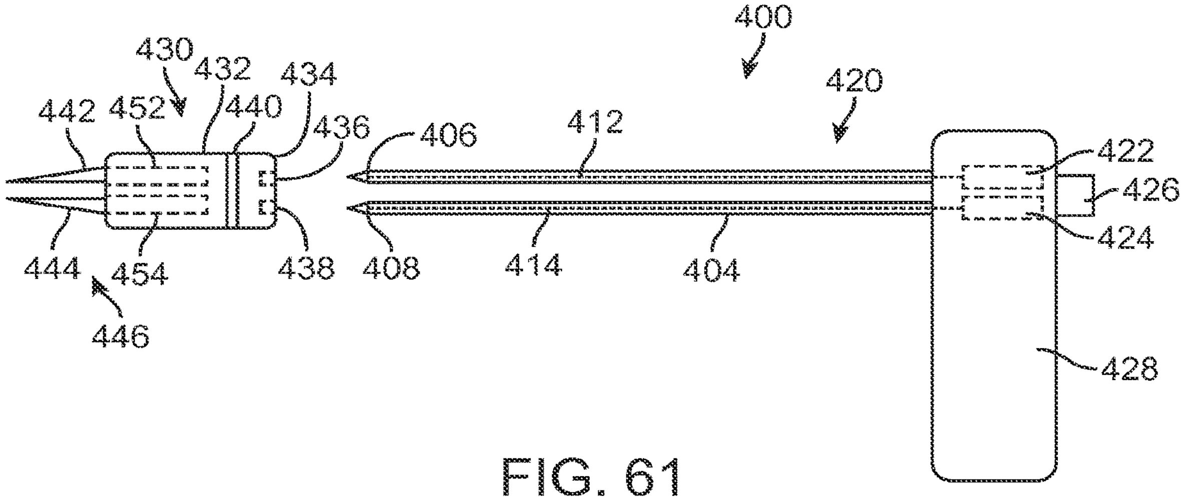
FIGS. 61-62 illustrate a modular laparoscopic tool that has a proximal assembly with a plurality of small diameter shafts that extend distally from a common handle and an attachable/detachable working tip.
Figure 62:
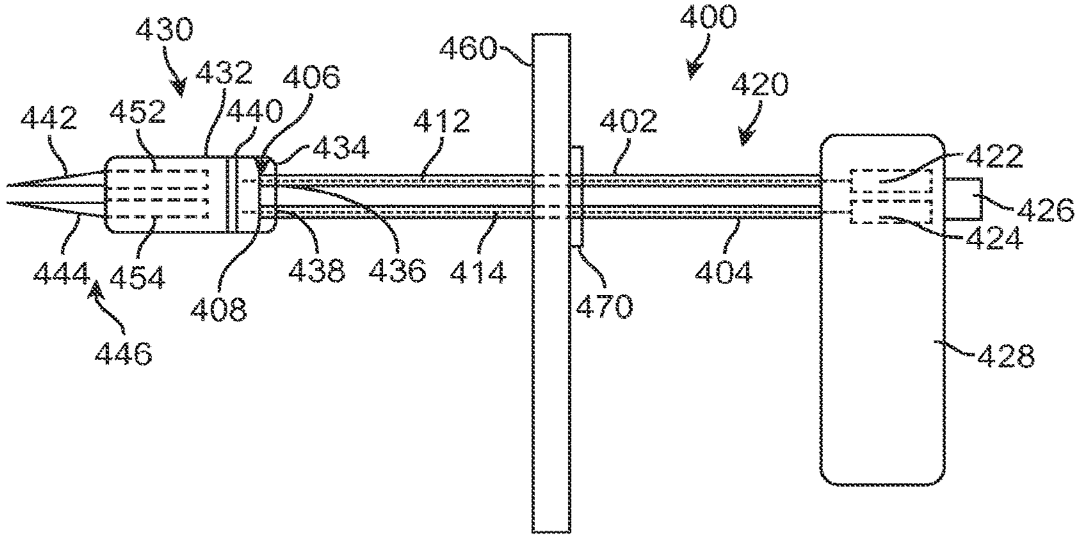

FIGS. 61-62 illustrate a modular laparoscopic tool 400 that is adaptable for use in manual or robotic-controlled hybrid NOTES procedures according to the present invention. The modular laparoscopic tool 400 has a proximal assembly 420 and an attachable/detachable working tip 430. The proximal assembly 420 includes a plurality of small diameter shafts 402, 404 that extend distally from a common handle 428. There will typically be two, three or four of the small diameter shafts 402, 404, however more may be used if necessary for operating the working tip 430 or for operating more than one working tip 430 by a single proximal assembly 420. The small diameter shafts 402, 404 will preferably have a diameter of 1 millimeter or less. The small diameter shafts 402, 404 will preferably be made of a rigid, high-strength material, for example stainless steel, cobalt-chromium alloy or titanium alloy or a reinforced composite material, such as a carbon fiber composite. For laparoscopic use, the length of the small diameter shafts 402, 404 will typically be from 20 to 40 cm, but other lengths can be used, particularly for other surgical approaches. The small diameter shafts 402, 404 may be solid or one or more of the small diameter shafts 402, 404 may be tubular to accommodate one or more control members 412, 414 running through the hollow shafts 402, 404. The control members 412, 414 may be mechanical (e.g. rods or cables that push, pull and/or rotate), electrical (to deliver electrical energy and/or control signals), pneumatic, hydraulic, etc. Alternatively or in addition, the small diameter shafts 402, 404 themselves may push, pull, rotate and/or deliver electrical energy and/or control signals. Control signals may also be transmitted wirelessly or through an umbilical cable.

The handle 428 may be adapted for manual control with one or more control input devices 426 (e.g. buttons, knobs, sliders, trackballs, joysticks, triggers, etc.) for controlling the operation of the working tip 430. Alternatively or in addition, the handle 428 may be adapted for connection to a robotic surgical system, as described above. As another alternative, the handle 428 may utilize remote control technology to create a manually-controlled, fly-by-wire laparoscopic tool. Voice controls may also be combined with the manual or robotic-controlled embodiments.

The working tip 430 will typically have an end effector 446, shown here as a pair of grasper or needle holder jaws 442, 444, although any of the surgical tools listed above in Table 1 may be implemented. Optionally, the working tip 430 may have a tip body 432 and a connector body 434 that are connected to one another by a wrist mechanism 440 that provides rotation and/or angulation of the end effector 446 with respect to the small diameter shafts 402, 404 of the proximal assembly 420. Alternatively or in addition, the small diameter shafts 402, 404 may form part of a bar mechanism for actuation and/or movement and angulation of the working tip 430. As shown in FIG. 62, the working tip 430 can be connected to the proximal assembly 420 by inserting the distal ends of the small diameter shafts 402, 404 into a like number of sockets 436, 438 on the connector body 434. One or more detents or a locking mechanism, as described above, may be used to secure the working tip 430 to the small diameter shafts 402, 404. Optionally, an indicator light or other indicator means may be used to indicate that a proper connection has been established.

The motive power for operating the working tip 430 may reside in the handle 428 and may be transmitted to the working tip 430 through one or more of the small diameter shafts 402, 404. For example, the handle 428 may include one or more motors and/or rotary or linear actuators 422, 424 connected to the working tip 430 by way of the small diameter shafts 402, 404 and/or control members 412, 414. In this case, the working tip 430 will have one or more actuator mechanisms 452, 454 (e.g. gears, cams, bar mechanism, etc.) for translating the linear and/or rotary motion of the small diameter shafts 402, 404 and/or control members 412, 414 into the desired motion of the end effector 446.

Alternatively, the motive power for operating the working tip 430 may reside in the working tip 430 itself. For example, the actuator mechanisms 452, 454 in the working tip 430 may be one or more motors and/or rotary or linear actuators that are controlled by the control input devices 426 on the handle 428 or by a robotic surgical system. The control signals may be transmitted through the small diameter shafts 402, 404, wirelessly or through an umbilical cable. Electrical power may be supplied by a battery on board the working tip 430 or it may be supplied through the small diameter shafts 402, 404, wirelessly or through an umbilical cable.

In use, the small diameter shafts 402, 404 will be inserted through the skin and the thoracic or abdominal wall 460 through individual punctures, as shown in FIG. 62. This greatly reduces the trauma to the patient compared to laparoscopic tools that use a single larger-diameter shaft. Convalescence time and the risk of herniation will be minimized. Optionally, the small diameter shafts 402, 404 may have sharpened distal tips 406, 408, as shown in FIG. 61, for piercing the patient's skin and underlying tissues. Alternative, the punctures through the skin may be formed using a needle or a small diameter trocar or stylet. A puncture tool may be provided with the proper number of needles or stylets and the correct spacing to introduce the small diameter shafts 402, 404 through the tissue. Optionally, the sharpened distal tips 406, 408 may be retractable or removable. In another alternative shown in FIG. 62, the conical portion of the sharpened distal tips 406, 408 may open up to form engagement members that secure the distal ends of the small diameter shafts 402, 404 to the working tip 430 and optionally transmit control actuation to the end effector 446.

Figure 63:
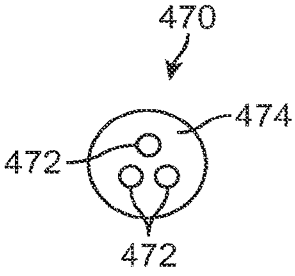
FIG. 63 shows a shaft alignment template for use with the modular laparoscopic tool of FIGS. 61-62.

FIG. 63 shows an optional shaft alignment template 470 for use with the modular laparoscopic tool 400 of FIGS. 61-62. The alignment template 470 has a preferably flat body 474 with a plurality of alignment holes 472 equal in number to the number of small diameter shafts 402, 404. FIG. 63 shows an example of a shaft alignment template 470 made for a modular laparoscopic tool 400 with three small diameter shafts. The outer shape of the shaft alignment template 470 can be round, oval, square, triangular or any practical or esthetically pleasing shape. The alignment holes 472 are sized for a close sliding fit around the small diameter shafts 402, 404 and are spaced to maintain the alignment of the small diameter shafts 402, 404 as they enter and pass through the skin. The alignment template 470 can be made of a metal, polymer or composite material that can be sterilized for use in a surgical setting. Optionally, a transparent or translucent polymer may be used so as not to obscure the surgeon's view of the patient's skin underneath the alignment template 470.

In use, the shaft alignment template 470 is placed against the patient's skin, as shown in FIG. 62, and optionally held in place with a contact adhesive. The distal ends 406, 408 of the small diameter shafts 402, 404 are aligned with the holes 472 and pushed through the skin. The shaft alignment template 470 assures that the small diameter shafts 402, 404 will be properly aligned and correctly spaced for attachment to the working tip 430 after they have passed through the thoracic or abdominal wall 460.

The working tip 430, or a plurality of working tips 430, are preferably inserted through a NOTES delivery tool, such as an endoscope overtube as described above, and advanced to the surgical site. The working tip 430 is then connected to the proximal assembly 420 within the body cavity for performing surgery, as shown in FIG. 62. The working tips 430 may be exchanged as needed during the surgical procedure. When the surgery is done, the working tip 430 is disconnected from the proximal assembly 420. The working tip or tips 430 are withdrawn from the body through the NOTES delivery tool or directly through the natural orifice that it was delivered through. The NOTES delivery tool is withdrawn through the natural orifice where it was inserted. If any internal incisions were made for surgical access, a suture device may be used to close the internal incisions, for example using a purse string suture. A purse string suture can also be placed earlier in the procedure and used to seal the internal incision around the NOTES delivery tube during the procedure, then used to close the incision when the tube is withdrawn. The small diameter shafts 402, 404 are withdrawn from the body, leaving only small puncture wounds that generally will not require sutures or any other tissue closure device.

While the present invention has been described herein with respect to the exemplary embodiments and the best mode for practicing the invention, it will be apparent to one of ordinary skill in the art that many modifications, improvements and subcombinations of the various features and embodiments, adaptations and variations can be made to the invention without departing from the spirit and scope thereof.

What is claimed is:

1. A surgical tool system comprising:

a surgical tool shaft having a distal end configured to be advanced through a laparoscopic port into a location within a patient's body and a proximal end configured to remain outside of the patient's body;

a handle attached to the proximal end of the shaft;

a magnetizable surgical tool tip detachably connectable to the distal end of the surgical tool shaft;

a latch on the shaft for selectively engaging the surgical tool tip; and a magnet on the shaft configured to attract the surgical tool tip and align said tip with the shaft, wherein the surgical tool tip is positioned to be mechanically engaged by the shaft after magnetic alignment.

* * * * *